(12) United States Patent
Jang

(10) Patent No.: US 11,618,901 B2
(45) Date of Patent: Apr. 4, 2023

(54) ANTI-MIRNA CARRIER CONJUGATED WITH A PEPTIDE BINDING TO A CANCER CELL SURFACE PROTEIN AND USE THEREOF

(71) Applicant: UNIVERSITY—INDUSTRY COOPERATION GROUP OF KYUNG HEE UNIVERSITY, Gyeonggi-do (KR)

(72) Inventor: Hyeung Jin Jang, Seoul (KR)

(73) Assignee: UNIVERSITY—INDUSTRY COOPERATION GROUP OF KYUNG HEE UNIVERSITY, Gyeonggi-do (KR)

( * ) Notice: Subject to any disclaimer, the term of this patent is extended or adjusted under 35 U.S.C. 154(b) by 0 days.

(21) Appl. No.: 17/371,289

(22) Filed: Jul. 9, 2021

(65) Prior Publication Data

US 2022/0135978 A1 May 5, 2022

(30) Foreign Application Priority Data

May 12, 2020 (KR) ........................ 10-2020-0056569

(51) Int. Cl.
*C12N 15/113* (2010.01)
*A61K 48/00* (2006.01)

(52) U.S. Cl.
CPC ...... *C12N 15/1135* (2013.01); *A61K 48/0008* (2013.01); *C12N 2310/141* (2013.01)

(58) Field of Classification Search
CPC ....................... C12N 15/1135; C12N 2310/141
See application file for complete search history.

(56) References Cited

U.S. PATENT DOCUMENTS

2016/0081944 A1* 3/2016 Lee ..................... C12N 15/111
424/491
2017/0189550 A1* 7/2017 Álvarez Puebla ..... A61K 45/06

FOREIGN PATENT DOCUMENTS

KR    10-2007-0095882 A    10/2007
KR       10-1667649 B1     10/2016

OTHER PUBLICATIONS

Hu et al. (Biomaterials (2013) 34(37):9496-9508). (Year: 2013).*
Alessandro Bertucci et al., "Tumor-Targeting, MicroRNA-Silencing Porous Silicon Nanoparticles for Ovarian Cancer Therapy" ACS Appl. Mater. Interfaces 2019, 11, 23926-23937.
Yunching Chen et al., "In vivo delivery of miRNAs for cancer therapy: Challenges and strategies" Adv Drug Deliv Rev. Jan. 2015; 81: 128-141.
Yanhui Lou et al., "MicroRNA-21 promotes the cell proliferation, invasion and migration abilities in ovarian epithelial carcinomas through inhibiting the expression of PTEN protein", International Journal of Molecular Medicine 26: 819-827, 2010.
European Commission, "MIRNANO Report Summary" 2019, 1-4.

* cited by examiner

*Primary Examiner* — J. E. Angell
(74) *Attorney, Agent, or Firm* — Harness, Dickey & Pierce, P.L.C.

(57) ABSTRACT

The present disclosure relates to an anti-miRNA delivery system, and more specifically, relates to a technique of using a cancer-targeting anti-miRNA delivery system including porous silicon nanoparticles containing anti-miRNA to which a cancer cell surface protein-binding peptide is conjugated, for use in treating cancer. As a result of intensive studies in order to use and apply anti-miR-21 oligonucleotides to the treatment of ovarian cancer, the present inventors confirmed for the first time that when porous silicon nanoparticles containing an anti-miRNA-21 oligonucleotide to which a specific cancer cell surface protein-binding peptide is conjugated are applied, apoptosis is induced in an ovarian cancer cell line and cell viability is reduced, thus, an anti-miRNA delivery system, which is the aforementioned conjugate, is expected to be usefully used as a platform for treating various cancers, especially for treating ovarian cancer.

4 Claims, 22 Drawing Sheets

Specification includes a Sequence Listing.

```
                       SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: cancer cell surface protein binding peptides

<400> SEQUENCE: 1

Cys Gly Lys Arg Lys
1               5

<210> SEQ ID NO 2
<211> LENGTH: 22
<212> TYPE: DNA
<213> ORGANISM: Artificial Sequence
<220> FEATURE:
<223> OTHER INFORMATION: anti-miRNA-21

<400> SEQUENCE: 2
tcaacatcag tctgataagc ta                                            22
```

ANTI-MIRNA CARRIER CONJUGATED WITH A PEPTIDE BINDING TO A CANCER CELL SURFACE PROTEIN AND USE THEREOF

CROSS-REFERENCE TO RELATED APPLICATION

This application claims priority to and the benefit of Korean Patent Application No. 2020-0056569, filed on May 12, 2020, the disclosure of which is incorporated herein by reference in its entirety.

FIELD

The present disclosure discloses an anti-miRNA delivery system, and more specifically, discloses a technique of using a cancer-targeting anti-miRNA delivery system including porous silicon nanoparticles containing anti-miRNA to which a cancer cell surface protein-binding peptide is conjugated, for use in treating cancer.

BACKGROUND miRNAs are short endogenous non-coding RNAs that regulate gene expression at the post-transcriptional level by suppressing RNA translation or inducing the degradation of a target RNA transcript, and they play a central role in regulating major cellular processes, including cell metabolism, differentiation, proliferation and apoptosis. Further, dysregulation and abnormal expression of a specific miRNA called oncomiR are known to be associated with the early development and progression stages of cancer.

Accordingly, anti-miRNA therapy may induce anti-cancer effects by silencing upregulated oncomiRs using antisense oligonucleotides, and more specifically, may be used as a strategy for treating cancer by allowing a single miRNA to continuously induce additional beneficial effects if the single miRNA suppresses a specific oncomiR by simultaneously targeting different messenger RNAs (mRNAs) and regulating multiple biological pathways.

Meanwhile, as a strong correlation between miRNA signature and cancer development has become more established, several anti-miR therapies have been deployed against various animal cancer models, including breast cancer, lung cancer, and lymphoma (Korean Patent Registration No. 10-1667649), but studies on its application to ovarian cancer have been insufficient.

SUMMARY

As a result of intensive studies in order to use and apply anti-miR-21 oligonucleotides to the treatment of cancer, the present inventors confirmed for the first time that when porous silicon nanoparticles containing an anti-miRNA-21 oligonucleotide to which a specific cancer cell surface protein-binding peptide is conjugated are applied, apoptosis is induced in an ovarian cancer cell line and cell viability is reduced, thereby completing the present disclosure based on this.

Thus, an object of the present disclosure is to provide a cancer-targeting anti-miRNA delivery system including: a cancer cell surface protein-binding peptide; and porous silicon nanoparticles (pSiNP) containing anti-miRNA.

Further, another object of the present disclosure is to provide a pharmaceutical composition for treating cancer, including the cancer-targeting anti-miRNA delivery system.

In addition, still another object of the present disclosure is to provide a method for preparing a cancer-targeting anti-miRNA delivery system, the method including: 1) loading anti-miRNA into porous silicon nanoparticles by mixing the anti-miRNA, a $CaCl_2$) solution, and porous silicon nanoparticles; and 2) modifying the surface of the porous silicon particles of the product of 1) with a cancer cell protein-binding peptide.

However, a technical problem to be achieved by the present disclosure is not limited to the aforementioned problem, and other problems that are not mentioned may be clearly understood by a person skilled in the art from the following description.

To achieve the objects of the present disclosure as described above, the present disclosure provides a cancer-targeting anti-miRNA delivery system including:

a cancer cell surface protein-binding peptide; and porous silicon nanoparticles (pSiNP) containing anti-miRNA.

As an exemplary embodiment of the present disclosure, the cancer cell surface protein-binding peptide may include an amino acid sequence represented by SEQ ID NO: 1.

As another exemplary embodiment of the present disclosure, the cancer cell surface protein-binding peptide may bind to a cancer cell surface protein p32.

Further, the present disclosure provides a pharmaceutical composition for treating cancer, including the cancer target anti-miRNA delivery system as an active ingredient.

In addition, still another object of the present disclosure is to provide a method for preparing a cancer-targeting anti-miRNA delivery system, the method including: 1) loading anti-miRNA into porous silicon nanoparticles by mixing the anti-miRNA, a $CaCl_2$) solution, and porous silicon nanoparticles; and 2) modifying the surface of the porous silicon particles of the product of 1) with a cancer cell protein-binding peptide.

Furthermore, the present disclosure provides a method for treating cancer, the method including administering the pharmaceutical composition to an individual.

Further, the present disclosure provides a use of the pharmaceutical composition for treating cancer.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION

Figure 1A:
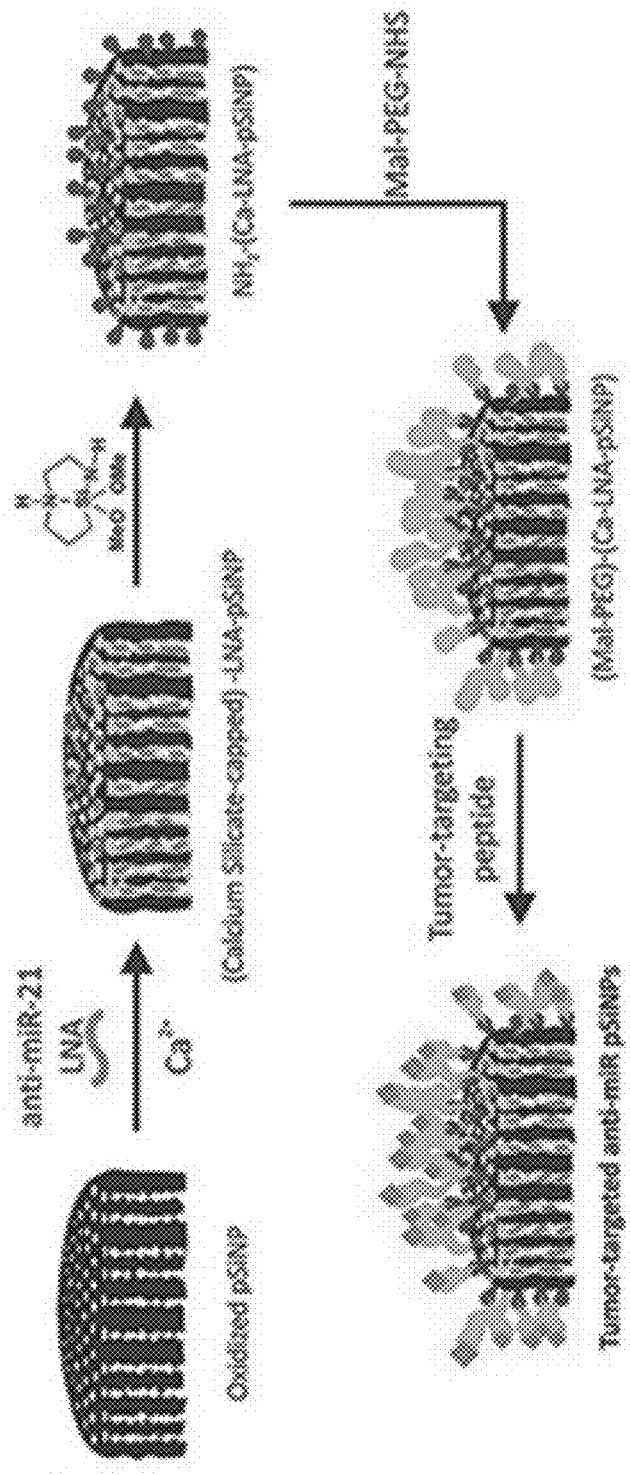
FIG. 1A schematically illustrates a procedure for loading anti-miRNA oligonucleotides into porous silicon nanoparticles, and then attaching PEG and a cancer cell surface protein-binding peptide group thereto.

Hereinafter, the present disclosure will be described in detail.

As a result of intensive studies in order to use and apply anti-miR-21 oligonucleotides to the treatment of cancer, the present inventors confirmed that when porous silicon nanoparticles containing an anti-miRNA-21 oligonucleotide to which a specific cancer cell surface protein-binding peptide is conjugated are applied, apoptosis is induced in an ovarian cancer cell line and cell viability is reduced, thereby completing the present disclosure based on this.

As used herein, the term "cancer" refers to a disease that forms a mass or tumor consisting of undifferentiated cells that proliferate indefinitely in a tissue, ignoring order, and is a generic term for a group of diseases which can ultimately infiltrate and destroy surrounding normal tissues and organs and metastasize from a primary lesion to any organ of an individual to create a new place of growth.

As used herein, the "ovarian cancer" refers to a cancer which develops in an ovary, and ovarian cancer is broadly divided into epithelial cell carcinoma, germ cell tumors, and stromal tumors depending on the tissue in which the cancer develops, and among them, ovarian epithelial cell carcinoma that develops from epithelial cells on the surface of an ovary accounts for 90% or more of all ovarian cancer types.

Although the exact cause of ovarian cancer is not yet known, DNA mutations have been identified as a major factor in increasing the risk of developing ovarian epithelial cancer, which is the most common form of ovarian cancer.

The most common symptoms of ovarian cancer are pelvic pain or abdominal pain, and urinary tract symptoms such as urgency and urinary frequency, and other possible symptoms include fatigue, dyspepsia, lower back pain, dyspareunia, constipation, changes in menstrual pattern.

Meanwhile, in an exemplary embodiment of the present disclosure, a free cysteine on a candidate cancer cell surface protein-binding peptide forms a covalent thioether bond with an anti-miR-21-loaded pSiNP via maleimide, so it was confirmed that the cancer cell surface protein-binding peptide is conjugated to the anti-miR-21-loaded porous silicon nanoparticles (see Example 1).

In addition, in another exemplary embodiment of the present disclosure, a significant reduction (about 70%) in the relative expression of miR-21 was confirmed by comparing OAW42 cells treated with anti-miR-21 CGKRK (SEQ ID NO: 1)-pSiNP and untreated cells, and it was confirmed that OAW42 cells to which anti-miR-21 CGKRK (SEQ ID NO: 1)-pSiNP was applied showed the highest Caspase-3 activity, and as a result, the most significant apoptosis was induced and viability was decreased most significantly (see Example 2).

Furthermore, the present inventors confirmed that in ovarian cancer cell lines (CAOV-3, COV-318, OVCAR-8, Kuramochi, KF-28, and IGROV-1) other than OAW42 cells, CGKRK (SEQ ID NO: 1) was an optimal cancer cell surface protein-binding peptide, and that anti-miR-21 CGKRK (SEQ ID NO: 1)-pSiNP reduced the viability of the ovarian cancer cell lines (see Example 3).

Further, in still another exemplary embodiment of the present disclosure, the in vivo efficacy of the anti-miR-21 CGKRK (SEQ ID NO: 1)-pSiNP was confirmed using COV-318 xenograft tumors subcutaneously transplanted into nude mice, and more specifically, it was confirmed that the cancer cell surface protein-binding peptide CGKRK (SEQ ID NO: 1) improved the accumulation of nanoparticles in tumors and suppressed the growth of tumors excised from mice administered anti-miR-21 CGKRK (SEQ ID NO: 1)-pSiNP.

Through the example results, the present inventors propose a use of the anti-miRNA CGKRK (SEQ ID NO: 1)-pSiNP for delivering anti-miRNA and a use thereof for treating cancer.

Thus, the present disclosure provides a cancer targeting anti-miRNA delivery system including: a cancer cell surface protein-binding peptide; and porous silicon nanoparticles (pSiNP) containing anti-miRNA, and a pharmaceutical composition for treating cancer, including the cancer targeting anti-miRNA delivery system as an active ingredient, and preferably provides a pharmaceutical composition for treating ovarian cancer.

As used herein, the term "cancer cell surface protein-binding peptide" refers to a new promising treatment tool against potential tumors, which targets cancer cells more effectively and have fewer side effects than cancer therapies in the related art.

The cancer cell surface protein-binding peptide not only accurately targets unregulated signaling pathways, but also exhibits high potential for the aggressive treatment of cancer due to its specificity of targeting a unique or overexpressed receptor on cancer cells.

The cancer cell surface protein-binding peptide not only may deliver a drug by binding to a target or act as an antagonist to various ligands, but also may provide an additional therapeutic option alone or in a combined therapy when some unique anticancer activity is given.

In the present disclosure, the cancer cell surface protein-binding peptide may include an amino acid sequence represented by SEQ ID NO: 1.

In this case, it is possible to include an amino acid sequence having a sequence homology of 70% or more, preferably 80% or more, more preferably 90% or more, and most preferably 95%, 96%, 97%, 98%, or 99% or more with the amino acid sequence represented by SEQ ID NO: 1.

In addition, the cancer cell surface protein-binding peptide according to the present disclosure can target a tumor cell by binding to a protein that is abnormally abundantly expressed on the surface of the tumor cell, and may preferably target a tumor cell by binding to a cancer cell surface protein p32, but is not limited thereto.

As used herein, the term "p32 protein" is a protein located in mitochondria in normal cells, but is a protein which is abnormally expressed on the cell surface in tumor cells.

As used herein, the term "microRNA (miRNA)" refers to a small RNA that serves to control gene expression in an organism.

The miRNA is widely known by studies on nematodes, and it is known that there are hundreds of miRNAs even in the human body.

As the name implies, miRNAs are smaller in size than existing RNAs.

An ordinary mRNA consists of thousands of nucleotides, whereas a miRNA consists of 20 to 25 nucleotides.

Ribonucleic acid (RNA) is known to play a role in delivering genetic information of DNA and transporting amino acids, and a base sequence of DNA having genetic information is transferred to mRNA as it is, and then a protein is synthesized again via tRNA of ribosomes present in the cytoplasm.

As it has been found that miRNA complementarily binds to mRNA in this process to act as a central regulator in the process of intracellular gene expression, miRNA is assumed to have various and essential functions as a new form of bioregulator.

As used herein, the term "locked nucleic acid (LNA)" is a locked nucleic acid (LNA) often referred to as inaccessible RNA, and is a RNA nucleotide whose ribose moiety is modified with an extra bridge linking 2' oxygen and 4' carbon.

The bridge "fixes" ribose in the form of 3 'endo' (North), which is often found in an A-type double helix.

Furthermore, the LNA binds to a target with excellent affinity and specificity and is known to one of the most advanced tools for microRNA silencing because an artificial back bone is highly resistant to nucleolytic degradation.

The present disclosure discloses a locked nucleic acid (LNA) against microRNA 21 (miR-21) as an anti-miRNA, but is not limited thereto, and as used herein, the term "anti-miRNA" is used interchangeably with a superordinate concept or the same concept of the term "locked nucleic acid (LNA)".

In the present disclosure, the anti-miR-21 oligonucleotide sequence is as follows:

5'-TCAACATCAGTCTGATAAGCTA-3 (SEQ ID NO: 2), where the sequence of an LNA oligonucleotide is shown in italics.

In this case, it is possible to include a base sequence having a sequence homology of 70% or more, preferably 80% or more, more preferably 90% or more, and most preferably 95% or more with the base sequence.

The porous silicon nanoparticles according to the invention may be biodegradable, but are not limited thereof, the porous silicon nanoparticles containing the anti-miRNA may be those in which the cancer cell surface protein-binding peptide is conjugated to porous silicon nanoparticles, and preferably, the cancer cell surface protein-binding peptide may be conjugated to nanoparticles by forming a covalent thioether bond with a free cysteine on the peptide via maleimide, but is not limited thereto.

As used herein, the term "treatment" refers to all actions that ameliorate or beneficially change symptoms caused by ovarian cancer by administering the pharmaceutical composition according to the present disclosure.

The pharmaceutical composition may further include a pharmaceutically acceptable carrier.

The pharmaceutically acceptable carrier is typically used in the formulation of a drug, and may be one or more selected from the group consisting of lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, and the like, but is not limited thereto.

The pharmaceutical composition may further include one or more selected from the group consisting of a diluent, an excipient, a lubricant, a wetting agent, a sweetener, a flavoring agent, an emulsifier, a suspending agent, a preservative and the like, which are typically used in the preparation of the pharmaceutical composition, in addition to the aforementioned ingredients.

The pharmaceutical composition may be administered orally or parenterally.

In the case of parenteral administration, the pharmaceutical composition or the active ingredient may be administered by intravenous injection, subcutaneous injection, intramuscular injection, peritoneal injection, endothelial administration, local administration, intranasal administration, intrapulmonary administration, rectal administration, or the like.

As used herein, the term "pharmaceutically effective amount" refers to an amount of an active ingredient capable of exhibiting a pharmaceutically meaningful effect.

A pharmaceutically effective amount of the active ingredient for a single dose may be prescribed in various ways depending on factors, such as formulation method, administration method, age, body weight, sex or disease condition of the patient, diet, administration time, administration interval, administration route, excretion rate and response sensitivity.

For example, the pharmaceutically effective amount of the pharmaceutical composition according to the present disclosure for a single dose may range from 0.0001 to 200 mg/kg, 0.001 to 100 mg/kg, or 0.02 to 10 mg/kg, but is not limited thereto.

Further, the present disclosure provides a method for treating cancer, the method including administering, to an individual, a pharmaceutical composition for treating cancer, including a cancer-targeting anti-miRNA delivery system including: a cancer cell surface protein-binding peptide; and porous silicon nanoparticles (pSiNP) containing anti-miRNA, and preferably, provides a method for treating ovarian cancer, the method including administering, to an individual, a pharmaceutical composition for treating ovarian cancer, including a cancer-targeting anti-miRNA delivery system including: a cancer cell surface protein-binding peptide; and porous silicon nanoparticles (pSiNP) containing anti-miRNA.

The individual subjected to treatment may be a mammal, for example, a primate including a human, a monkey, and the like, a rodent including a mouse, a rat, and the like, or a cell or tissue isolated from the living organism thereof.

In an example, the subject is a mammal suffering from ovarian cancer, for example, a primate including a human, a monkey, and the like, a rodent including a mouse, a rat, and the like, or a cell or tissue isolated from the living organism thereof.

A pharmaceutical composition for treating cancer, including the above pharmaceutical composition or a cancer-targeting anti-miRNA delivery system including: a cancer cell surface protein-binding peptide; and porous silicon nanoparticles (pSiNP), as active ingredients, preferably a pharmaceutical composition for treating ovarian cancer may be formulated in the form of a solution in an oil or aqueous medium, a suspension, a syrup or an emulsion, or formulated in the form of an extract, an acida, a powder, granules, a tablet, a capsule, or the like, and may further include a dispersant or a stabilizer for formulation.

Meanwhile, in a specific exemplary embodiment of the present disclosure, it was confirmed that i) for LNA loading, via a series of reactions including performing reactions by mixing porous silicon nanoparticles (pSiNP), an LNA stock solution and a CaCl$_2$) solution, anti-miR-21 was loaded into a porous structure of the porous silicon nanoparticles (pSiNP), and ii) a free cysteine on a candidate cancer cell surface protein-binding peptide forms a covalent thioether bond with an anti-miR-21 loaded-pSiNP via maleimide, thereby conjugating the cancer cell surface protein-binding peptide to the anti-miR-21-loaded porous silicon nanoparticles.

The aforementioned process i) serves to make sure that the anti-miR-21 oligonucleotide is efficiently contained in the porous structure of the nanoparticles, but is not limited thereto.

Thus, as another aspect of the present disclosure, the present disclosure provides provide a method for preparing a cancer-targeting anti-miRNA delivery system, the method including: 1) loading anti-miRNA into porous silicon nanoparticles by mixing the anti-miRNA, a CaCl$_2$) solution, and porous silicon nanoparticles; and 2) modifying the surface of the porous silicon particles of the product in 1) with a cancer cell protein-binding peptide.

Hereinafter, preferred examples for helping the understanding of the present disclosure will be suggested. However, the following examples are provided only to more easily understand the present disclosure, and the contents of the present disclosure are not limited by the following examples.

EXAMPLES

Example 1. Experimental Materials and Experimental Methods

Example 1-1. Method for Preparing Porous Silicon Nanoparticles pSiNPs were prepared according to the published "perforation etching" procedure.

In short, highly boron-doped p+2-type crystalline silicon wafers (about 1 mΩ cm resistance, 100 mm diameter, Virginia Semiconductor, Inc.) were electrochemically etched in an electrolyte consisting of 3:1 (v:v) 48% aqueous hydrofluoric acid (HF):ethanol.

An etching waveform consisted of a square wave in which a lower current density of 46 mA cm$^{-2}$ was applied for 1.818 seconds, followed by a higher current density pulse of 365 mA cm$^{-2}$ applied for 0.363 seconds.

Further, the repetition of the waveform for 140 cycles produced a layered porous silicon membrane having thin and highly porous "perforations" repeated at approximately every 200 nm through a porous layer.

Next, the membrane was removed from a silicon substrate by applying a current density pulse of 3.4 mA cm$^{-2}$ to an electrolyte consisting of 1:20 (v:v) 48% aqueous HF:ethanol for 150 seconds ("lift off").

Next, the free-standing membrane was fragmented into nanoparticles by ultrasonic treatment in ethanol overnight.

Finally, pSiNPs, which were measured by dynamic light scattering to have an average diameter of 182±6 nm, were dispersed in a 0.8 mM sodium tetraborate aqueous solution for 1 hour, and a thin film of silicon oxide was grown on the surface thereof.

After the reaction, the oxidized pSiNPs were collected by centrifugation and stored in 100% ethanol.

1-2. Methods for Measuring Characteristics of Porous Silicon Nanoparticles

A hydrodynamic diameter and ζ-potential were measured on a Zetasizer Zs90 (Malvern Instruments).

The size was measured by dispersing pSiNPs in deionized water, and a potential value was measured by dispersing pSiNPs in phosphate-buffered saline (PBS) with pH 7.4.

In addition, transmission electron microscope (TEM) images were obtained by a JEOL-1200EX II device.

Attenuated total reflection Fourier transform infrared (ATR-FTIR) spectra were obtained using a Thermo Scientific Nicolet 6700 instrument equipped with a Smart iTR diamond ATR fixture.

Furthermore, porous layer porosity was measured using SLIM (infiltration method), which is a non-destructive optical interferometer technique, for a spectroscopic solution.

Further, adsorption-desorption isotherms were obtained from dry particles at 77 K in ASAP 2020 instruments (Micromeritics).

In addition, a total pore volume was determined from the adsorption-desorption isotherms, and a pore size was determined using a Barrett-Joyner-Halenda (BJH) method.

Furthermore, infrared (IR) spectra were obtained as attenuated total reflectance Fourier-transform infrared spectra (ATR-FTIR) from a dry powder nanoparticle sample.

1-3. Peptide Synthesis Method

Peptides were synthesized using an automated microwave assisted peptide synthesizer (Liberty; CEM, Matthews, NC) using standard solid-phase chemistry.

A peptide labeled with 5-fluorescein carboxylate (FAM) and having a 6-aminohexanoic acid spacer (X) for separating a dye from the sequence and an amide-blocked C-terminus was synthesized.

The cancer cell surface protein-binding peptides used were iRGD (sequence CRGDKGPDC (SEQ ID NO: 3)), iNGR (sequence CRNGRGPDC (SEQ ID NO: 4)), CGKRK (SEQ ID NO: 1) and t-LyP-1 (sequence CGNKRTR (SEQ ID NO: 6)), and CRA and CREK (SEQ ID NO: 5) peptides exhibited little or no targeting effect, and were used in control experiments.

The CREK peptide (sequence CREK) (SEQ ID NO: 5) was used in an in vitro experiment, whereas the CRA peptide (sequence CRA) was used in an in vivo experiment.

The CRA peptide was purchased from Genscript (Piscataway, N.J.).

1-4. Method for Preparing LNA-Loaded Porous Silicon Nanoparticles

A locked nucleic acid (LNA) oligonucleotide against miR-21 was synthesized by Qiagen (Hilden, Germany) and purified (HPLC purification).

The anti-miR-21 oligonucleotide sequence was as follows:

5'-TCAACATCAGTCTGATAAGCTA-3' (SEQ ID NO: 2) which is a locked nucleic acid (LNA) nucleotide, where the sequence of the LNA oligonucleotide is shown in italics.

A stock solution of 4 M calcium chloride ($CaCl_2$)) (MW=110.98, anhydrous, Spectrum Chemicals) was prepared in DNase-free water. For LNA loading, a solution in which 0.25 mg of pSiNPs was dispersed in 200 μL of ethanol in DNase-free water was mixed with 50 μL of a 150 μM LNA stock solution and 250 μl of a 4 M $CaCl_2$) solution. This provided a final concentration of 15 μM LNA (7.5 nmol), 0.25 mg of pSiNPs and 2 M $CaCl_2$) (in a solution of ethanol:DNase-free water of 1:1.5). The mixture was stirred at room temperature for 60 minutes and then centrifuged for 10 minutes. The pSiNPs were washed once with deionized water, once with 70% ethanol, and once with ethanol. For LNA loading, a Quasar 570-labeled anti-miR-21 oligonucleotide was used, and UV-vis absorption (λ=548 nm) of the supernatant was measured from each centrifugation step using a UV-vis spectrophotometer (SpectraMax Plus 384, Molecular Devices).

Since a final nanoparticle structure contains overcoating of polyethylene glycol (PEG) to improve circulation and one of various cancer cell surface protein binding-peptides for selective tissue homing, these cancer cell surface protein binding-peptides will be attached to Ca-LNA-pSiNP through a cyclic azasilane reagent (DMDASCO, 2,2-dimethoxy-1,6-diaza-2-silacyclooctane), which will produce a primary amine group on the particle surface through a ring-opening click reaction.

Figure 1B:
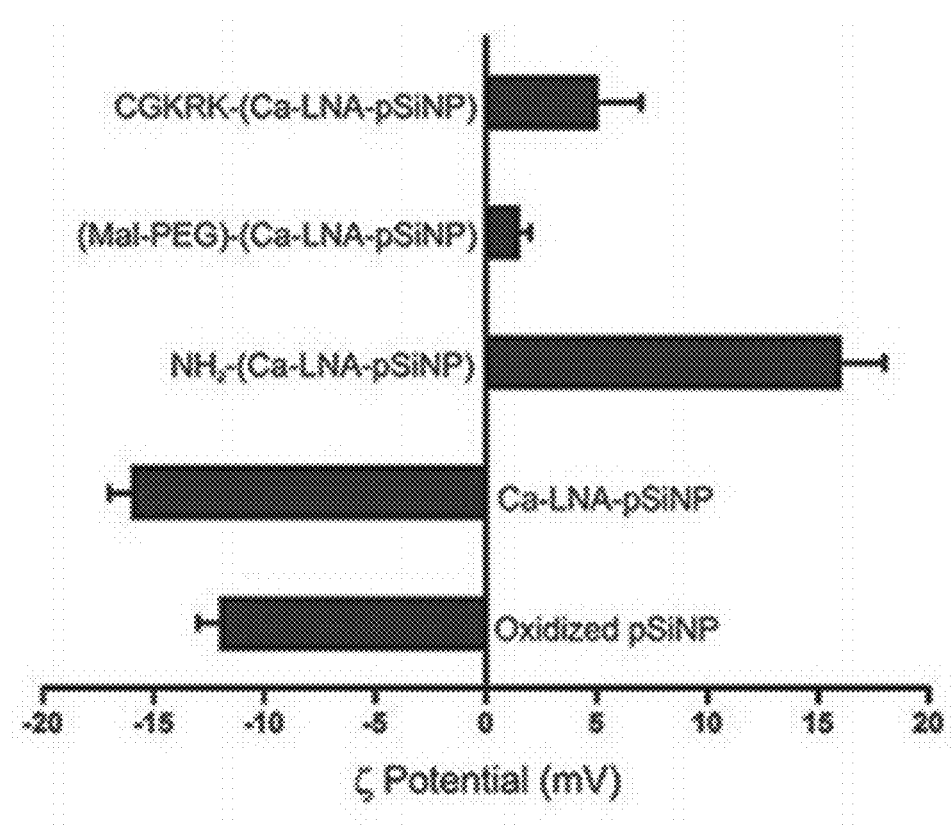
FIG. 1B illustrates the results of measuring ζ-potential in each functionalization step of preparing tumor-targeted anti-miR porous silicon nanoparticles (pSiNP)

The presence of the aforementioned amine linker is confirmed by the measurement of ζ-potential, and as illustrated in FIG. 1B, the shift to a positive value (+16±2 mV) was confirmed by Fourier transform infrared (FTIR) spectroscopy.

Using a calibration curve obtained from a standard solution of Quasar 570-labeled anti-miR-21 oligonucleotide at different concentrations, the above loading was measured to be 17% (evaluated by mass) corresponding to 28 nmol LNA/mg of porous silicon. Here, the loading value is defined as the mass of the loaded LNA divided by (the mass of the LNA loaded+the mass of the porous silicon) and multiplied by 100. Further, the efficiency of the loading procedure was calculated and found to be 97±2%.

In the aforementioned procedure, the hydrodynamic diameter of the nanoparticles increased slightly, and the ζ-potential became a more negative value.

Figure 1C:
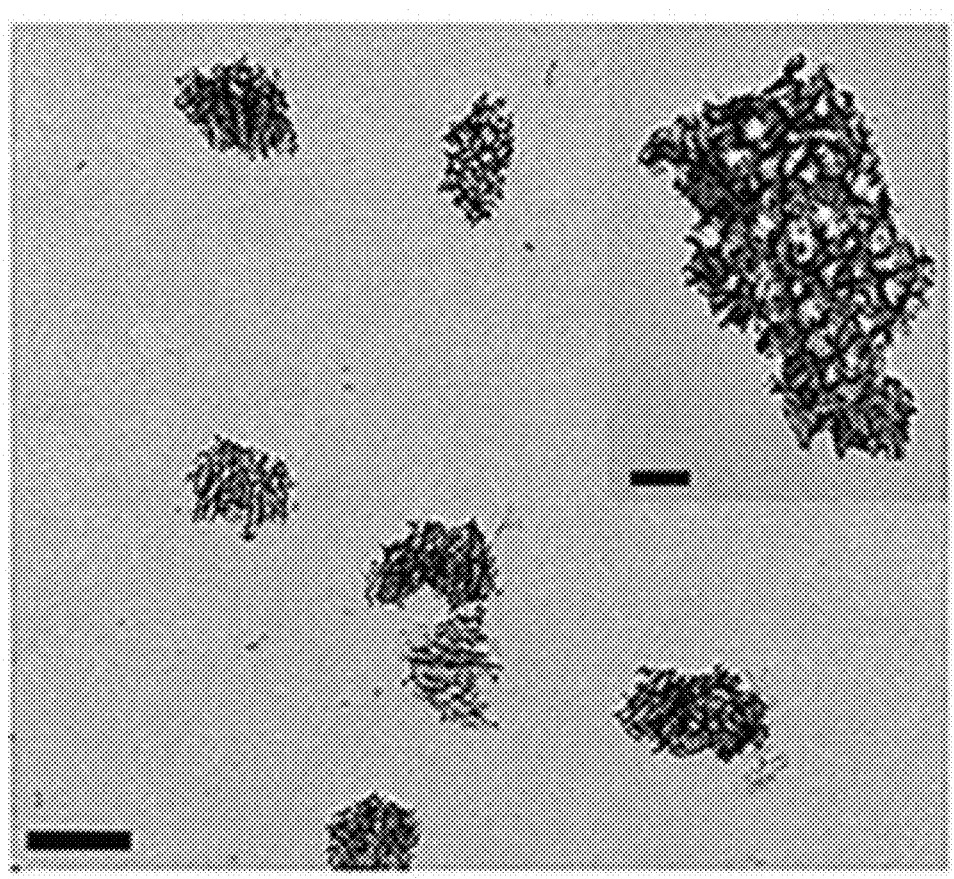
FIG. 1C illustrates a transmission electron microscope (TEM) image of unmodified porous silicon nanoparticles (pSiNP) to confirm the physical properties of the prepared tumor-targeted anti-miR pSiNP (scale bar=200 nm), and the inset illustrates the proximity of a single nanoparticle (scale bar=50 nm)
Figure 1D:
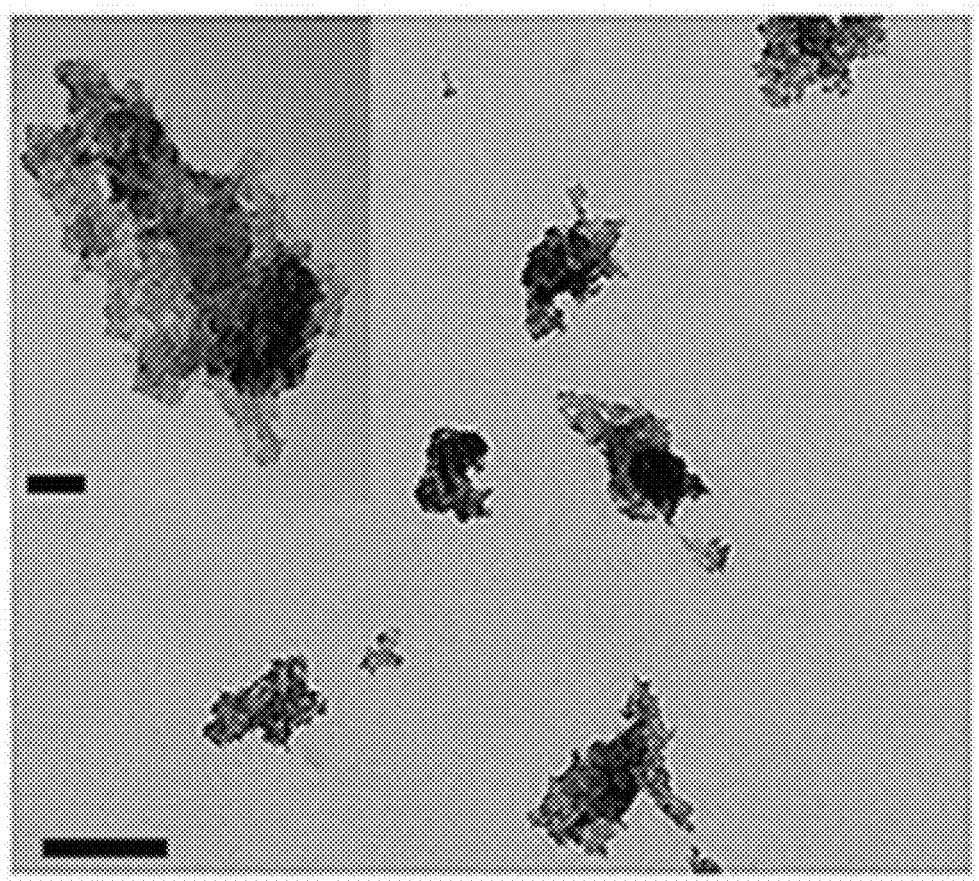
FIG. 1D illustrates a transmission electron microscope (TEM) image of calcium silicate capping porous silicon nanoparticles (pSiNP) of the prepared tumor-targeted anti-miR LNA pSiNP (scale bar=200 nm), and the inset illustrates the proximity of a single nanoparticle (scale bar=50 nm)
Figure 1E:
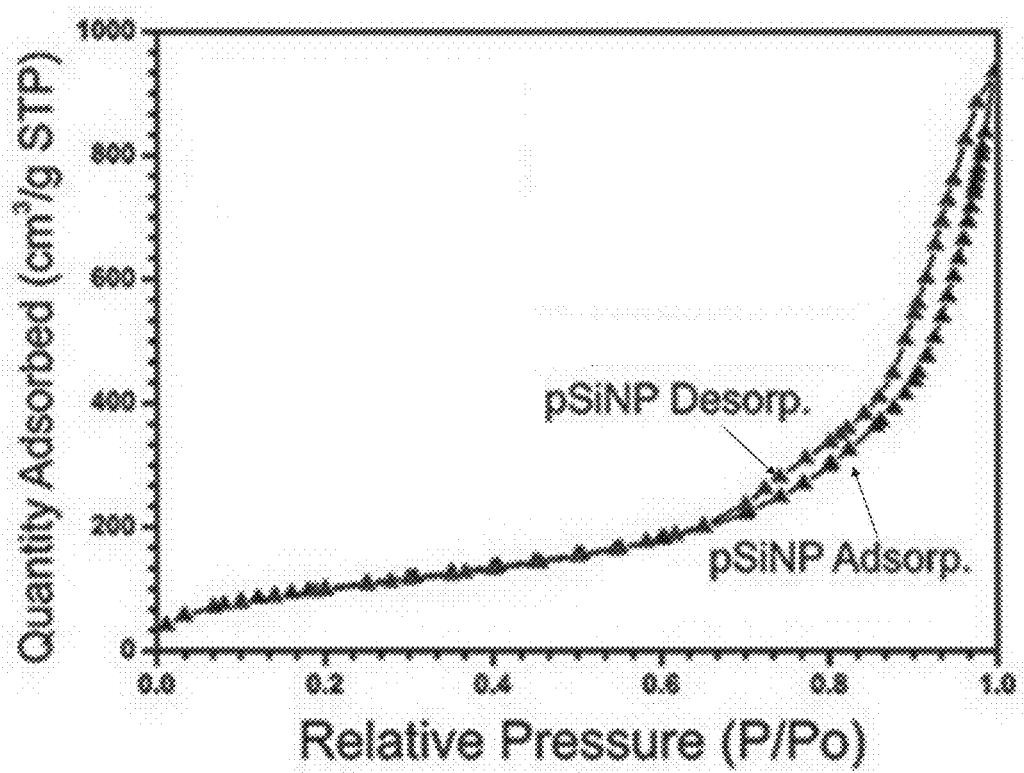
FIG. 1E illustrates a cryogenic adsorption-desorption isotherm of vacant unmodified porous silicon nanoparticles (PSiNP) of the prepared tumor-targeted anti-miR pSiNP.

In addition, as illustrated in FIG. 1C, it was confirmed that a porous nanostructure in a calcium silicate-trapped LNA-loading pSiNP (Ca-LNA-pSiNP) is less clear than an unmodified pSiNP. Furthermore, as illustrated in FIG. 1D, a morphology observed in a transmission electron microscope (TEM) image coincided with partially or completely sealed pores.

When a pSiNP having a scrambled LNA sequence, 5'-CATTAATGTCGGACAACTCAAT-3' is loaded, the same procedure as above was applied, where the sequence of the LNA oligonucleotide is shown in italics.

The same loading value was obtained for non-labeled LNA oligonucleotides as measured by a Nanodrop 2000 spectrophotometer (Thermo Scientific, ND-200).

A release profile of an oligonucleotide payload from a calcium silicate capped-pSiNP was obtained by dispersing 0.25 mg of pSiNPs loaded with a Quasar 570-labeled anti-miR-21 oligonucleotide in 1 mL of PBS, pH 7.4 and culturing the resulting dispersion at 37° C. with gentle shaking. The released labeled-oligonucleotide-containing supernatant was collected at different time points (1, 2, 4, 10, and 24 hours) and analyzed by optical absorbance spectroscopy ($\lambda$=548 nm).

The concentration of released oligonucleotide was determined using a calibration curve obtained from a standard solution of the same labeled oligonucleotide.

1-5. Method for Conjugating Cancer Cell Surface Protein-Binding Peptide to LNA-Loaded Porous Silicon Nanoparticles As illustrated in FIG. 1A, a candidate cancer cell surface protein-binding peptide was grafted onto nanoparticles via maleimide, which formed a covalent thioether bond with a free cysteine on the peptide.

First, the LNA-loaded pSiNPs (0.5 mg) were dispersed in 200 µL of dichloromethane (DCM), and 50 µL of a cyclic azasilane compound and 2,2-dimethoxy-1,6-diaza-2-silacyclooctane (DMDASCO) were added thereto.

Next, the mixture was cultured with gentle shaking at room temperature for 4 hours, and then centrifuged for 10 minutes, and the pSiNPs were washed once with DCM and twice with ethanol.

Next, aminated nanoparticles (NH2-LNA-pSiNP) were dispersed in a solution (180 µl) of ethanol (0.5 mg of nanoparticles in 80 µL of ethanol) and a heterologous functional linker maleimide-PEG-succinimidyl valerate (MAL-PEG-SVA).

Next, ethanol (MW=3400 in 5 mg/mL, Laysan Bio Inc.) was added thereto, the mixture was cultured overnight with gentle shaking at room temperature, and then the nanoparticles were separated by centrifugation for 10 minutes.

Next, the particles were redispersed in ethanol and centrifuged (3×) to remove an unbound PEG linker.

Next, peptide conjugation was obtained by aliquoting a stock solution (50 µL) containing a 0.6 m/mL peptide in deionized water and mixing the PEG-pSiNP (0.3 mg in 50 µL ethanol). After the mixture was reacted at room temperature for 4 hours, the particles were washed three times with ethanol (dispersed and then centrifuged) and finally dispersed in pure ethanol.

To avoid lysis during storage, a final formulation was stored in pure ethanol at 4° C., separated by centrifugation and resuspended in a PBS solution immediately before administration. This procedure was performed without process modification for all peptides described in the present study.

The density of the peptide conjugated to a pSiNP was measured using a FAM-labeled peptide by measuring the absorbance ($\lambda$=548 nm) of the supernatant and found to be 39±6 nmol peptide/mg pSiNP (n=15).

1-6. Cell Culture

CAOV-3, COV-318, OVCAR-8, Kuramochi, KF-28, IGROV-1 and OWA42 cell lines were obtained from ATCC (Manassas, Va.), and all were certified by the STS test at ATCC.

Human OAW42 and COV-318 cells were cultured in DMEM supplemented with 10% fetal bovine serum (FBS) and 1% penicillin/streptomycin (P/S) in a 5% $CO_2$ humidified incubator at 37° C.

Further, human CAOV-3, OVCAR-8, KF-28 and IGROV-1 cells were cultured in RPMI-1640 supplemented with 10% FBS and 1% P/S in a 5% $CO_2$ humidified incubator at 37° C.

In addition, human Kuramochi cells were cultured in RPMI-1640 supplemented with 10% FBS, a 1% non-essential amino acid (NEAA), 4.0 mg/mL human insulin and 1% P/S in a 5% $CO_2$ humidified incubator at 37° C.

Furthermore, healthy human LP-9 cells were cultured in Medium 199 (modified with Earle's salts and glutamine) supplemented with 15% FBS and 0.4 µg/mL hydrocortisone in a 5% $CO_2$ humidified incubator at 37° C.

Cells were passaged until they reached 80 to 90% confluency, and isolated using an enzyme-free dissociation buffer (Gibco, Thermo Fisher).

1-7. Method for Confirming Accumulation of Peptide-Functionalized Porous Silicon Nanoparticles in Cultured Cells After OAW42, COV-318, CAOV-3, OVCAR-8, KF-28, Kuramochi, IGROV-1 and LP-9 cells (about $5 \times 10^4$ each) were seeded in 24-well culture plates, 0.5 mL of a relevant culture medium (see 1-6) was added thereto, and the cells were allowed to grow overnight.

Cells using different FAM-labeled peptide-pSiNP formations were cultured in each well at a particle concentration of 0.025 mg/mL in a 5% $CO_2$ humidified incubator at 37° C. for 4 hours.

Next, the cells were harvested, washed three times with PBS, treated with 4% paraformaldehyde (PFA) in PBS (15 minutes, room temperature) and washed three times with PBS again.

Next, cell samples were analyzed by flow cytometry on an LSR Fortessa FACS analyzer (BD Biosciences), where the peptides used were iRGD, iNGR, CGKRK (SEQ ID NO: 1) and t-LyP-1.

In these experiments, a CREK peptide (SEQ ID NO: 5) was used as a "control" pSiNP.

The sequences of all the peptides are as described above (see 1-3). The nanoparticles were sealed with the same calcium silicate capping and surface functionalization chemistries as those which contain a DNA sequence that mimics the LNA and are used together with an anti-miR-21 LNA-containing sample.

1-8. Confocal Microscopic Image

After approximately $5 \times 10^4$ OAW42 cells were seeded onto square glass coverslips in a 6-well culture plate, 2 mL of a culture medium was added thereto, and the resulting mixture was cultured overnight.

Next, the cells were cultured in the presence of 0.05 mg/mL FAM-labeled CGKRK (SEQ ID NO: 1)-pSiNP loaded with a Quasar 570-labeled anti-miR-21 oligonucleotide for 4 hours.

Next, the cell samples were divided into two groups.

One group was fixed and finished immediately before confocal microscopy analysis, and the other was prepared for confocal microscopy analysis after discarding the nanoparticle-containing medium, and then culturing the cells in a new culture medium for an additional 24 hours.

Post-treatment of the cell samples is as follows:

The cell layer grown on the surface of the glass coverslip was (i) gently washed three times with PBS, (ii) fixed to 4% PFA in PBS (15 minutes, room temperature), and (iii) washed three times with PBS, (iv) treated with DAPI for nuclear staining (10 minutes, room temperature, protected from light), and (v) washed three times with PBS.

Finally, the coverslip was mounted on a microscope glass slide.

Confocal microscope images were obtained from Zeiss LSM 710 NLO using fluorescence excitation/emission filters for DAPI (cell nuclei), FAM (targeting peptide) and Cy3 (Quasar 570-labeled oligonucleotides).

1-9. In Vitro RT-qPCR

Using RT-qPCR, miR-21 expression was evaluated and knockdown efficiency was investigated.

OAW42 or COV-318 cells were cultured together with a free anti-miR-21 LNA (without porous nanoparticles), anti-miR-21 CGKRK (SEQ ID NO: 1)-pSiNP, an anti-miR-21 control CREK (SEQ ID NO: 5)-pSiNP, scrambled LNA CGKRK (SEQ ID NO: 1)-pSiNP, a commercial Lipofectamine formulation (RNAi Max, Thermo Fisher) loaded with anti-miR-21 (positive control) and a pure culture medium (negative control).

Here, "anti-miR-21 control CREK-pSiNP" refers to a pSiNP into which the correct anti-miR-21 LNA is loaded but containing a non-targeting control peptide CREK (SEQ ID NO: 5).

"Scrambled CGKRK-pSiNP" refers to a PSiNP into which a scrambled anti-miR-21 sequence is loaded but containing the correct CGKRK (SEQ ID NO: 1) cancer cell surface protein-binding peptide sequence.

All the cultures were administered so as to provide a total concentration of 100 nM LNA in the culture wells.

After culturing for 48 hours, cells were collected and total small RNA was extracted using a mirVana miRNA isolation kit according to the manufacturer's instructions (Thermo Fisher).

Further, TaqMan microRNA analysis was performed according to the manufacturer's protocol (ThermoFisher) in order to quantify miR-21 expression. According to the manufacturer's instructions, isolated RNA was first transcribed into cDNA (TaqMan microRNA reverse transcription kit, ThermoFisher).

Synthesized cDNA was applied to qPCR (TaqMan universal master mix II, Thermo Fisher), and miR-21 expression was quantified using Taqman probe technology, miR-21 (hsa-miR-21, analysis ID00397, Thermo Fisher) and U6 snRNA (analysis ID 001973, Thermo Fisher) as an internal control. PCR amplification was performed in a Stratagene Mx3005P qPCR system, and data was analyzed using a comparable $\Delta\Delta CT$ method.

1-10. Caspase Assay

After OAW42 cells were seeded into 24-well culture plates, 0.5 mL of a culture medium was added thereto, and the cells were allowed to grow overnight. The cells were cultured together with a free anti-miR-21 LNA (without porous nanoparticles), anti-miR-21 CGKRK (SEQ ID NO: 1)-pSiNP, an anti-miR-21 control CREK (SEQ ID NO: 5)-pSiNP, scrambled LNA CGKRK (SEQ ID NO: 1)-pSiNP, 2 µM camptothecin (positive control) and a pure culture medium (negative control).

All the cultures were administered so as to provide a total concentration of 100 nM LNA in the culture wells. After culturing for 48 hours, cell caspase-3 activity was measured using a caspase-3 fluorescence measurement analysis kit (Abcam) according to the manufacturer's instructions. The fluorescence intensity of the samples was measured on a Fluorolog-3 spectrophotometer (Horiba Scientific) using $\Delta ex/\Delta em 400/505$ nm.

1-11. Cell Viability Assay

Cell viability was measured by MTT analysis. In the case of model OAW42 cells, approximately $8\times10^3$ cells were seeded into a 96-well culture plate, and then 0.1 mL culture medium was added thereto, and the cells were cultured overnight.

Next, the cells were cultured together with a free anti-miR-21 LNA (without porous nanoparticles), anti-miR-21 CGKRK (SEQ ID NO: 1)-pSiNP, an anti-miR-21 control CREK (SEQ ID NO: 5)-pSiNP, scrambled LNA CGKRK (SEQ ID NO: 1)-pSiNP, DMSO 30% (positive control) and a pure culture medium (negative control).

Here, "anti-miR-21 control CREK-pSiNP" refers to a pSiNP into which the correct anti-miR-21 LNA is loaded but containing a non-targeting control peptide CREK (SEQ ID NO: 5).

"Scrambled CGKRK-pSiNP" refers to a PSiNP into which a scrambled anti-miR-21 sequence is loaded but containing the correct CGKRK (SEQ ID NO: 1) cancer cell surface protein-binding peptide sequence.

Different doses which provided a total concentration of 50, 100 or 200 nM LNA in the culture wells were applied to each formulation.

After culturing for 48 hours, MTT analysis was performed according to standard protocols, and cell samples were finally analyzed by optical absorption spectroscopy ($\lambda=570$ nm) using a UV-vis plate reader (SpectraMax Plus384, Molecular Devices).

MTT cell viability analysis was performed on COV-318, CAOV-3, OVCAR-8, KF-28, Kuramochi and IGROV-1 cells according to the same procedure; cells were cultured together with anti-miR-21 CGKRK (SEQ ID NO: 1)-pSiNP at a final LNA concentration of 200 nM.

1-12. Animal Model

All animal protocols have been approved by the Institutional Animal Care and Use Committee (IACUC) of Kyung Hee University, Republic of Korea (approval number: KHUASP (SE) –17-139). $2\times10^7$ COV-318 cells were subcutaneously inoculated into the right flank of female nude mice (6 weeks old) to produce a subcutaneous tumor xenograft model.

Next, when the tumor reached a volume of 50 mm$^3$ by monitoring the tumor size with a vernier caliper, mice were weighed and randomized into groups for subsequent targeting and therapeutic studies.

1-13. In Vivo Biodistribution

To investigate the distribution of PSiNPs in vivo, tumor-bearing mice were randomized into 3 groups (6 mice per group) as follows.

(i) Saline control, (ii) Quasar 670-labeled anti-miR-21 oligonucleotide payload, or (iii) Quasar 670-labeled anti-miR-21 oligonucleotide payload-loaded control CRA-pSiNP.

The mice were sacrificed 5 hours after injection, and major internal organs such as the lungs, heart, liver, spleen and kidneys were excised in addition to tumors, and analyzed by fluorescence imaging with IVIS 200 (Xenogen) using a Cy5.5filter acquisition window.

1-14. In Vivo Therapeutic Efficacy

Mice with tumors were randomized into 4 groups (6 or 7 mice per group) as follows and intravenously injected (tail vein, 25 mg/kg, corresponding to about 10 nmol of LNA per injection) when the tumor reached a volume of 50 mm$^3$.

(I) Saline control (7 rats), (ii) Anti-miR-21 CGKRK (SEQ ID NO: 1)-pSiNP (7 rats), (iii) Anti-miR-21 control CRA-pSiNP (6 rats) or (iv) Scrambled LNA CKRK-pSiNP (7 mice).

Tumor growth was evaluated by measuring tumor volume over the course of the process in which five injections were given on days 0, 1, 3, 5 and 7. Tumor volume is calculated as $V=(lw^2)/2$, where l is the length of the tumor measured in a living animal using a vernier caliper and w is the width.

At the end of the relevant timeline (day 10), mice were sacrificed and tumors were collected for visualization and gravimetric analysis. No mice were excluded from the analysis.

Here, the "PBS" is a negative control of tumor mice injected with saline, the "anti-miR-21 control pSiNP" is a pSiNP into which the correct anti-miR-21LNA is loaded but containing a non-targeting control peptide CRA, the "scrambled LNA CGKRK (SEQ ID NO: 1)-pSiNP" is a pSiNP containing the correct CGKRK (SEQ ID NO: 1) cancer cell surface protein-binding peptide sequence, but loaded with a scrambled anti-miR-21 sequence, and the "anti-miR-21 CGKRK (SEQ ID NO: 1)-pSiNP" is a candidate anticancer preparation.

To quantify treatment-related miR-21 knockdown, RT-qPCR was performed on tumor tissues collected from the mice on day 10 of a therapy consisting of relevant anti-miR-21 CGKRK (SEQ ID NO: 1)-pSiNP, anti-mir-21 control CRA-pSiNP and scrambled LNA CGKRK (SEQ ID NO: 1)-pSiNP formulations.

According to the manufacturer's instructions (Thermo Fisher), total small RNA was extracted from a flash-frozen tumor tissue using a mirVana isolation kit.

To quantify miR-21 expression, TaqMan micro-RNA analysis was performed according to the manufacturer's protocol (Thermo Fisher) and according to the above-described procedure for in vitro RT-qPCR. PCR amplification was analyzed using a comparable $\Delta\Delta CT$ method and normalized for tumor size.

1-15. Statistical Analysis

All of the above experiments were based on at least three independent replicates, and statistical analysis was performed using the two-tailed Student's test for two mean values or analysis of variance (ANOVA) and using a Bonferroni test for multiple values.

Example 2. Confirmation of Preparation that is Accumulated Most in OAW42 Cells and Confirmation of Silencing of miR-21 by Applying pSiNP Preparation Containing Various Peptides Peptides are attractive targeting elements because they are relatively small in size and generally do not induce immunogenic reactions, and their synthetic and chemical modification procedures are well established, and presentation of multiple copies of the peptide can significantly increase binding strength to the target on single nanoparticles, and previous studies have established that pSiNPs can be selectively targeted to a specific tissue using a peptide-based ligand.

2-1. Confirmation of Nanoparticle Preparation that is Accumulated Most in OAW42 Cells by Applying pSiNP Preparation Containing Various Peptides The present inventors observed in vitro cell targeting, miRNA silencing and therapeutic effects of nanoparticles according to the invention using an OAW42 human ovarian cancer cell line.

More specifically, a small library of anti-miR psiNPs functionalized with different cancer cell surface protein-binding peptides was prepared, and an attempt was made to identify a formulation that provides the highest nanoparticle accumulation.

The following peptides were used in the present example. iRGD, iNGR, CGKRK (SEQ ID NO: 1) and cleaved LyP-1 (t-LyP-1) (see 1-3).

Theses peptides have been proven to be respectively involved in different targeting pathways and to exhibit tumor-homing and tumor-penetrating properties, but have never been used as active ligands for targeting ovarian cancer by adhering to a pSiNP.

In addition, for comparison, the present inventors further used CREK (SEQ ID NO: 5), which is a control, as a mutant of a peptide showing no targeting activity in cell culture in the experiment of the present example.

According to the conjugation procedure described above (see 1-5), the FAM-labeled peptide (FAM is fluorescent label 5 carboxyfluorescein) was coupled to a PEGylated, anti-miR-loaded pSiNP.

Next, OAW42 cells were cultured together with different peptide-pSiNP preparations and the accumulated preparation was quantified by flow cytometry.

Figure 2A:
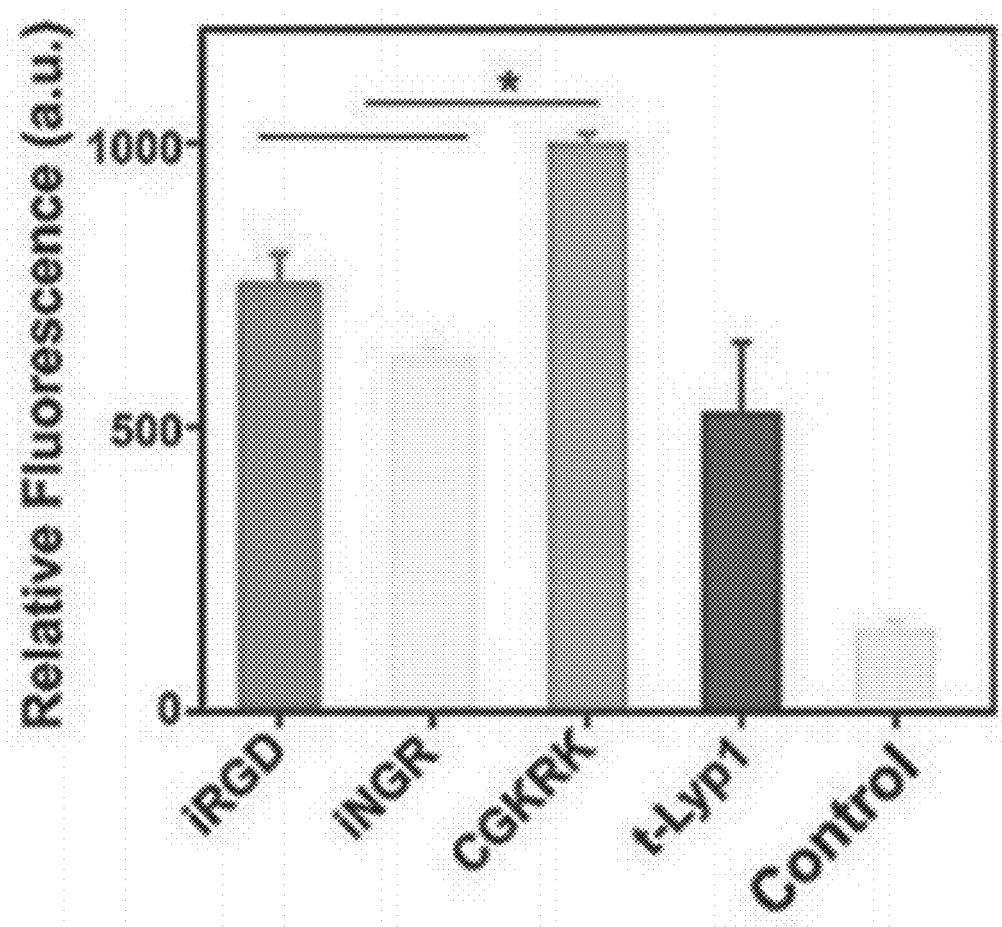
FIG. 2A illustrates the results of flow cytometry for evaluating the efficiency of a cell targeting group of the anti-miR-21pSiNP to localize the pSiNP in OAW42 cells in a model OAW42 ovarian cancer cell line.

As a result, as illustrated in FIG. 2A, CGKRK (SEQ ID NO: 1)-pSiNP showed the largest accumulation of nanoparticles in OAW42 cells.

Figure 3A:
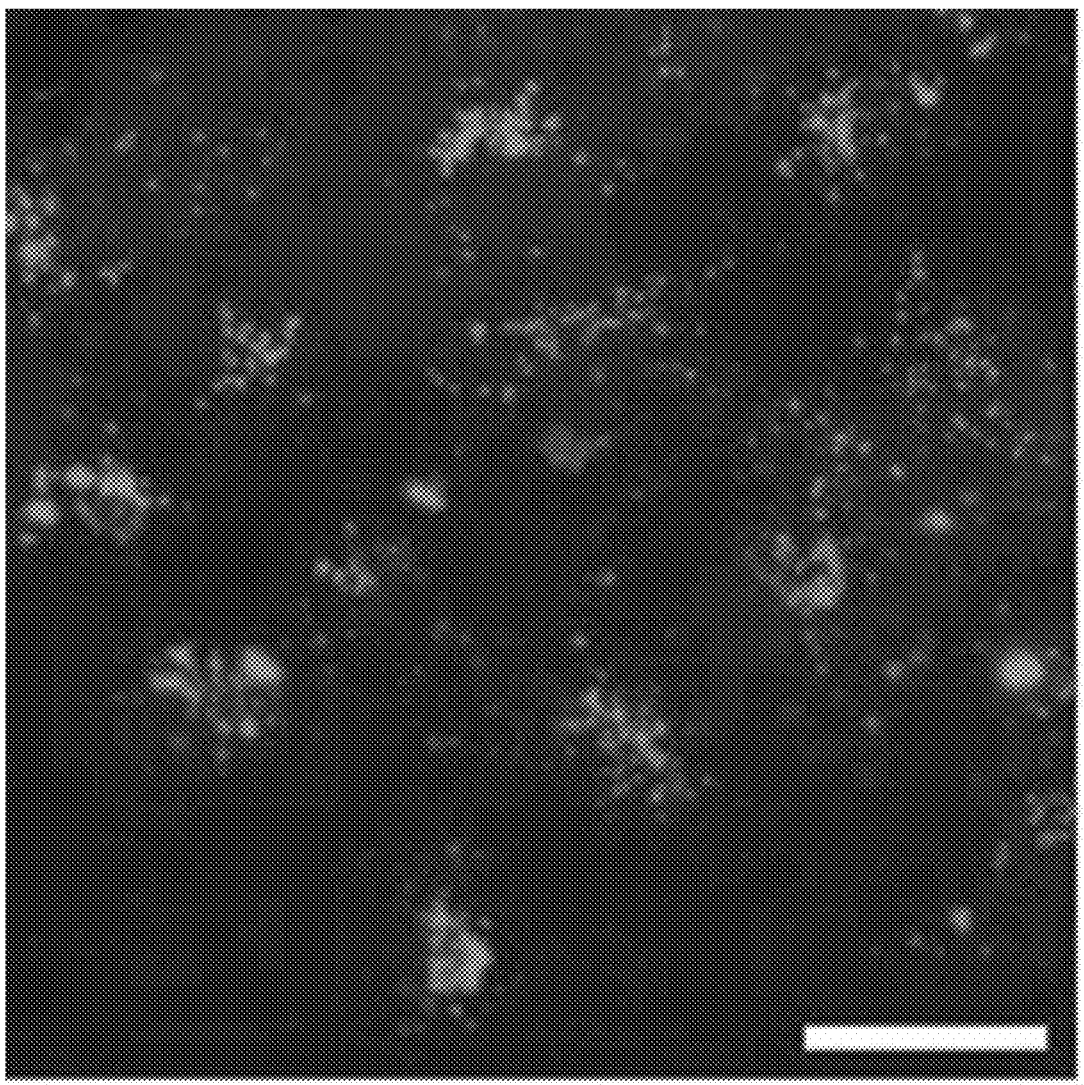
FIG. 3A illustrates the results of confirming a confocal microscopic image of OAW42 cells cultured together with (FAM-labeled)-CGKRK (SEQ ID NO: 1) (SEQ ID NO: 1) pSiNP into which Quasar 570-labeled anti-miR-21 oligonucleotides are loaded to confirm a red fluorescence emission image of the Quasar 570-labeled anti-miR-21 oligonucleotides.
Figure 3B:
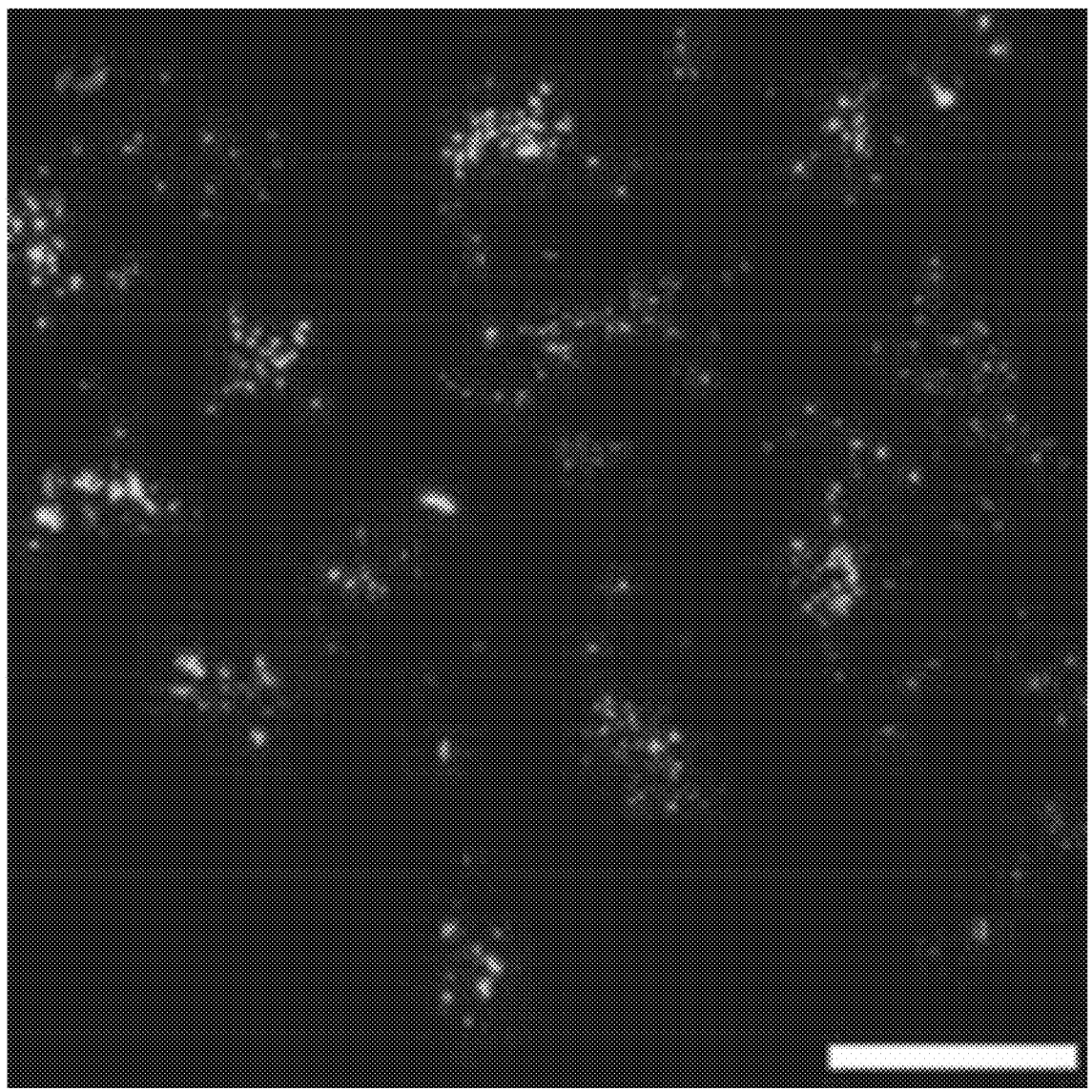
FIG. 3B illustrates the results of confirming a confocal microscopic image of OAW42 cells cultured together with (FAM-labeled)-CGKRK (SEQ ID NO: 1) (SEQ ID NO: 1)-pSiNP into which Quasar 570-labeled anti-miR-21 oligonucleotides are loaded to confirm a green fluorescence emission image of a FAM-labeled CGKRK (SEQ ID NO: 1) (SEQ ID NO: 1) peptide.
Figure 3C:
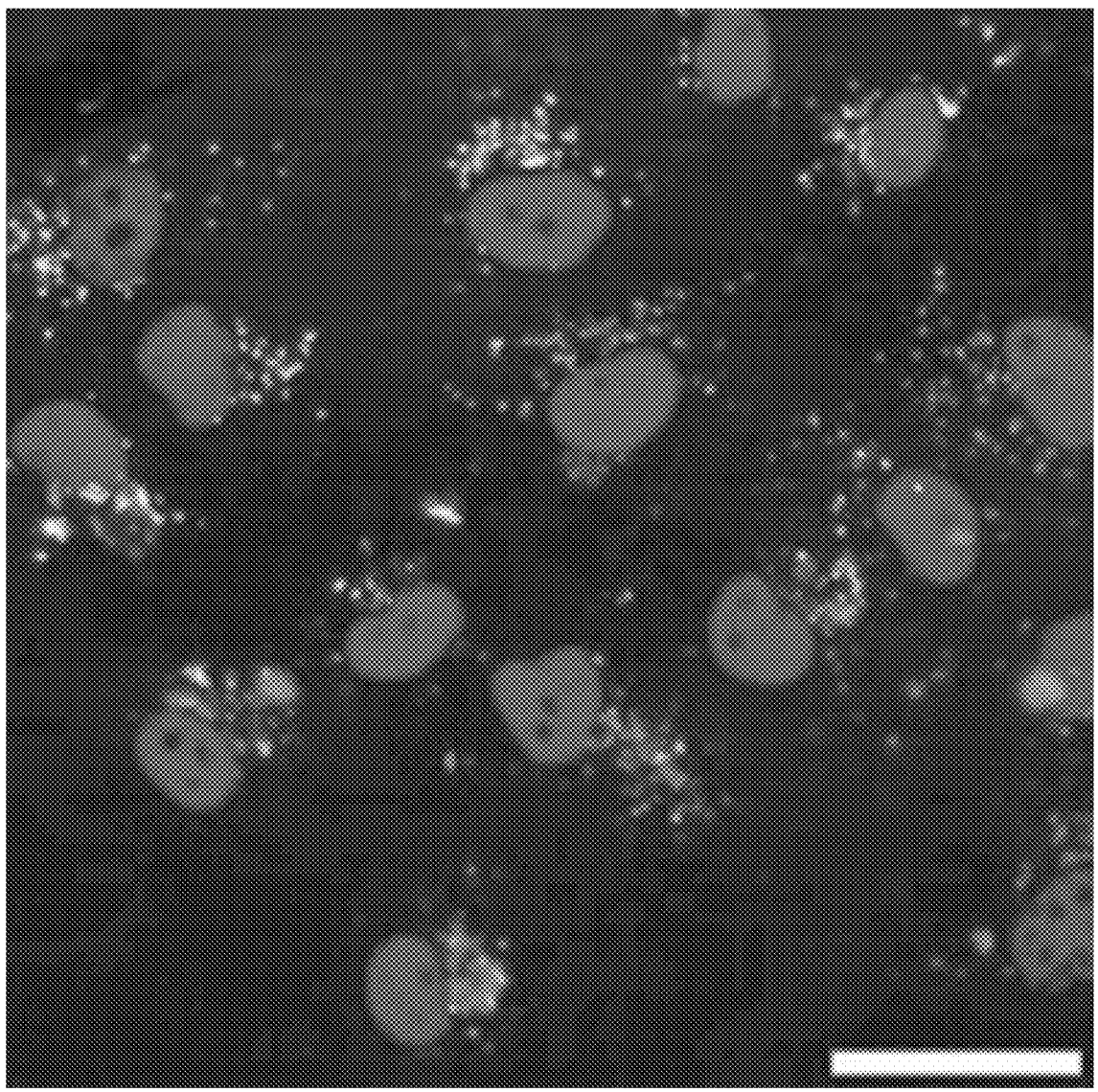
FIG. 3C illustrates the results of confirming a confocal microscopic image of OAW42 cells cultured together with (FAM-labeled)-CGKRK (SEQ ID NO: 1) (SEQ ID NO: 1)-pSiNP into which Quasar 570-labeled anti-miR-21 oligonucleotides are loaded to confirm a merged image of channels (a) and (b) by blue fluorescence emission of DAPI-stained cell nuclei.
Figure 3D:
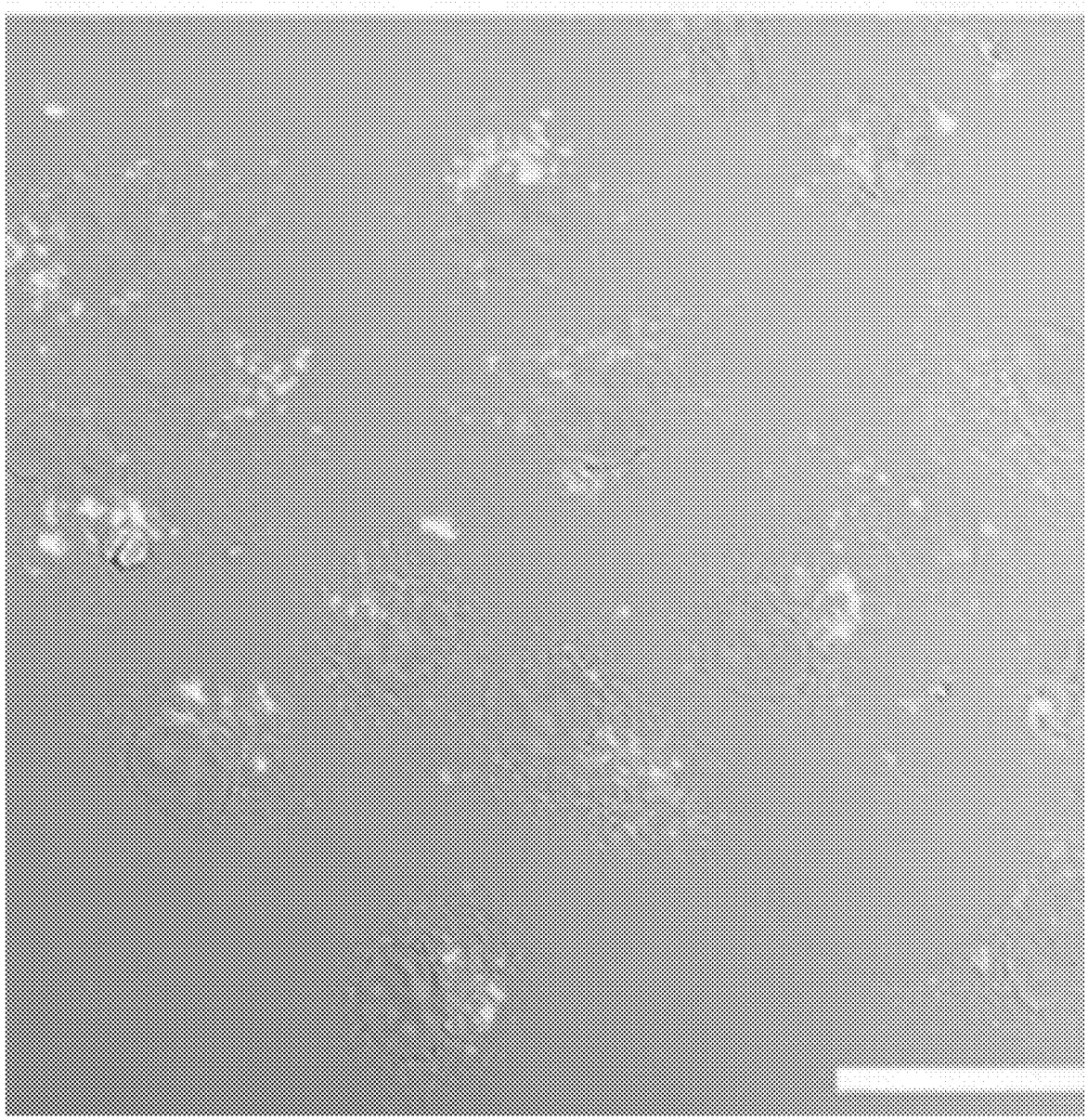
FIG. 3D illustrates a bright-field cell image combined with FIG. 3C.

Furthermore, as illustrated in FIG. 3C, confocal microscopy images of OAW42 cells cultured together with CGKRK (SEQ ID NO: 1)-pSiNP loaded with a Quasar 570-labeled oligonucleotide confirmed that FAM-labeled CGKRK (SEQ ID NO: 1) and oligonucleotide payloads after 24 hours were similarly located inside the cell.

2-2. Confirmation of Silencing of miR-21 in OAW42 Cells by Applying pSiNP Preparation Containing Various Peptides The silencing of microRNAs by released LNAs was evaluated by RT-qPCR analysis.

Figure 2B:
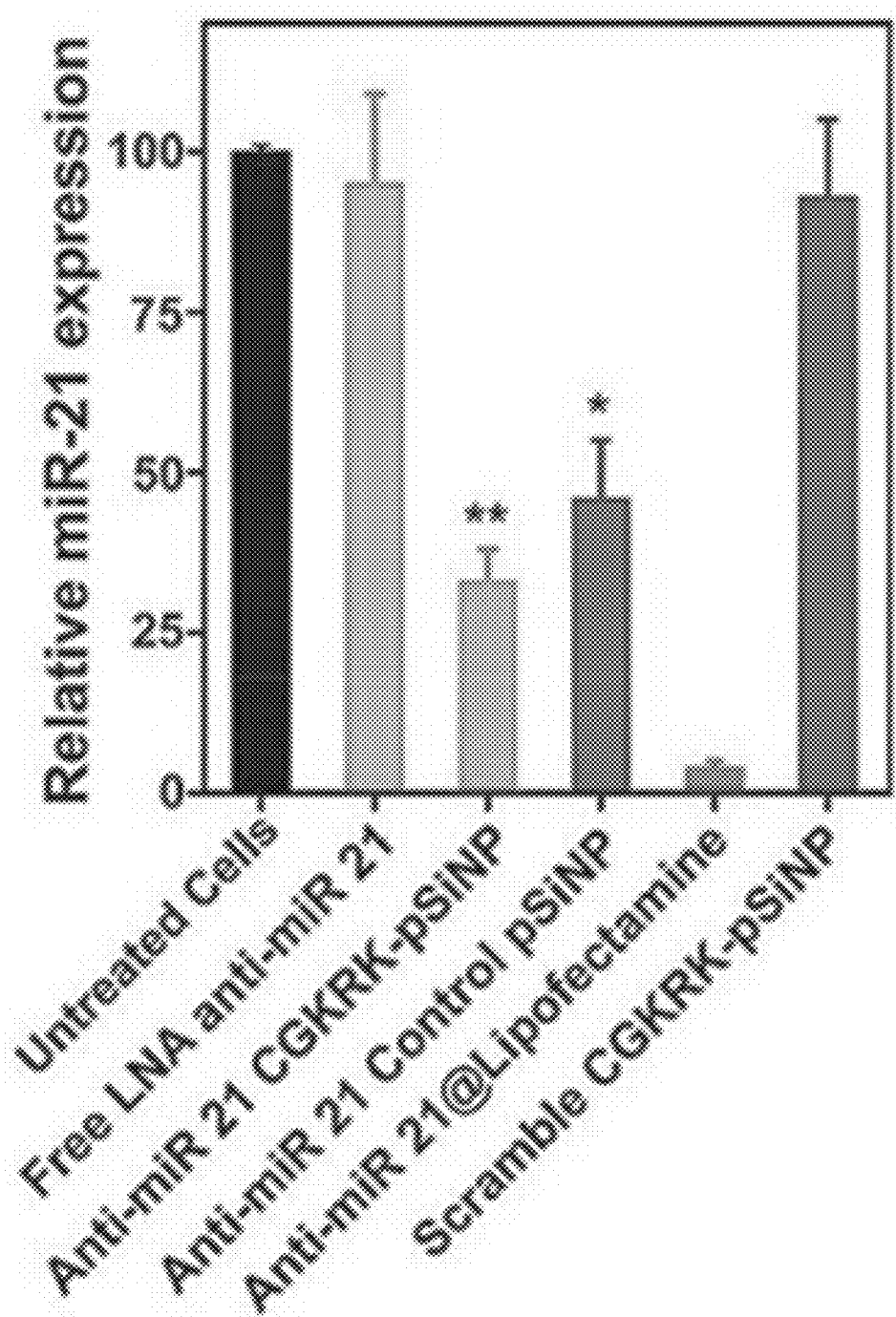
FIG. 2B illustrates relative miR-21 expression evaluated by RT-qPCR in OAW42 cells treated with a marked nanoparticle preparation to confirm microRNA silencing in a model OAW42 ovarian cancer cell line (mean±SD, n=6, * p<0.05, ** p<0.01)

As a result, as illustrated in FIG. 2B, a significant decrease (about 70%) in the relative expression level of miR-21 was confirmed by comparing the OAW42 cells treated with anti-miR-21 CGKRK (SEQ ID NO: 1)-pSiNP and the untreated cells.

The silencing effect of any non-specific microRNA was evaluated using CGKRK (SEQ ID NO: 1)-pSiNP loaded with a scrambled LNA sequence.

As a result, when compared with the cells of the control, no difference in the silencing effect of the microRNA was observed when CGKRK (SEQ ID NO: 1)-pSiNP loaded with the scrambled LNA sequence was administered. Similarly, administration of free-miR-21 LNA without pSiNP did not induce silencing of microRNA.

In addition, a control experiment was conducted using a CREK (SEQ ID NO: 5) control peptide instead of the cancer cell surface protein-binding peptide CGKRK (SEQ ID NO: 1) in pSiNP carrying anti-miR-21LNA. The cationic CREK (SEQ ID NO: 5) peptide was chosen because the peptide showed a substantially reduced level of in vitro cell targeting, as illustrated in FIG. 2A.

As a result, as illustrated in FIG. 2B, it was confirmed that the anti-miR-21 CREK (SEQ ID NO: 5)-pSiNP had a lower ability to suppress the expression of miR-21 than the nanoparticles modified with CGKRK (SEQ ID NO: 1) (about 55%).

From the above experimental results, it was confirmed that the CGKRK (SEQ ID NO: 1)-pSiNP preparation was accumulated most in OAW42 cells, and the present inventors selected an anti-miR pSiNP containing a tumor-homing peptide CGKRK (SEQ ID NO: 1) as a delivery system of anti-miR for treating ovarian cancer, based on the miR-21 silencing results obtained from OAW42 cells.

2-3. Confirmation of Apoptosis Caused by Silencing of miR-21

Since Caspase-3 is a marker of early apoptosis and can be used to evaluate whether apoptosis is induced by monitoring activation of the aforementioned marker, the present inventors conducted an experiment to confirm whether or not apoptosis was induced when anti-miR-21 CGKRK (SEQ ID NO: 1)-pSiNP was applied.

As a result, it was confirmed that OAW42 cells to which the anti-miR-21 CGKRK (SEQ ID NO: 1)-pSiNP was applied showed the highest Caspase-3 activity, that is, fluorescence emission triggered by the enzymatic activity of Caspase-3 on a fluorescent substrate. The activity level of Caspase-3 was similar to that observed in cells treated with camptothecin, which is a pro-apoptotic drug typically used as a positive control in Caspase analysis.

Figure 2C:
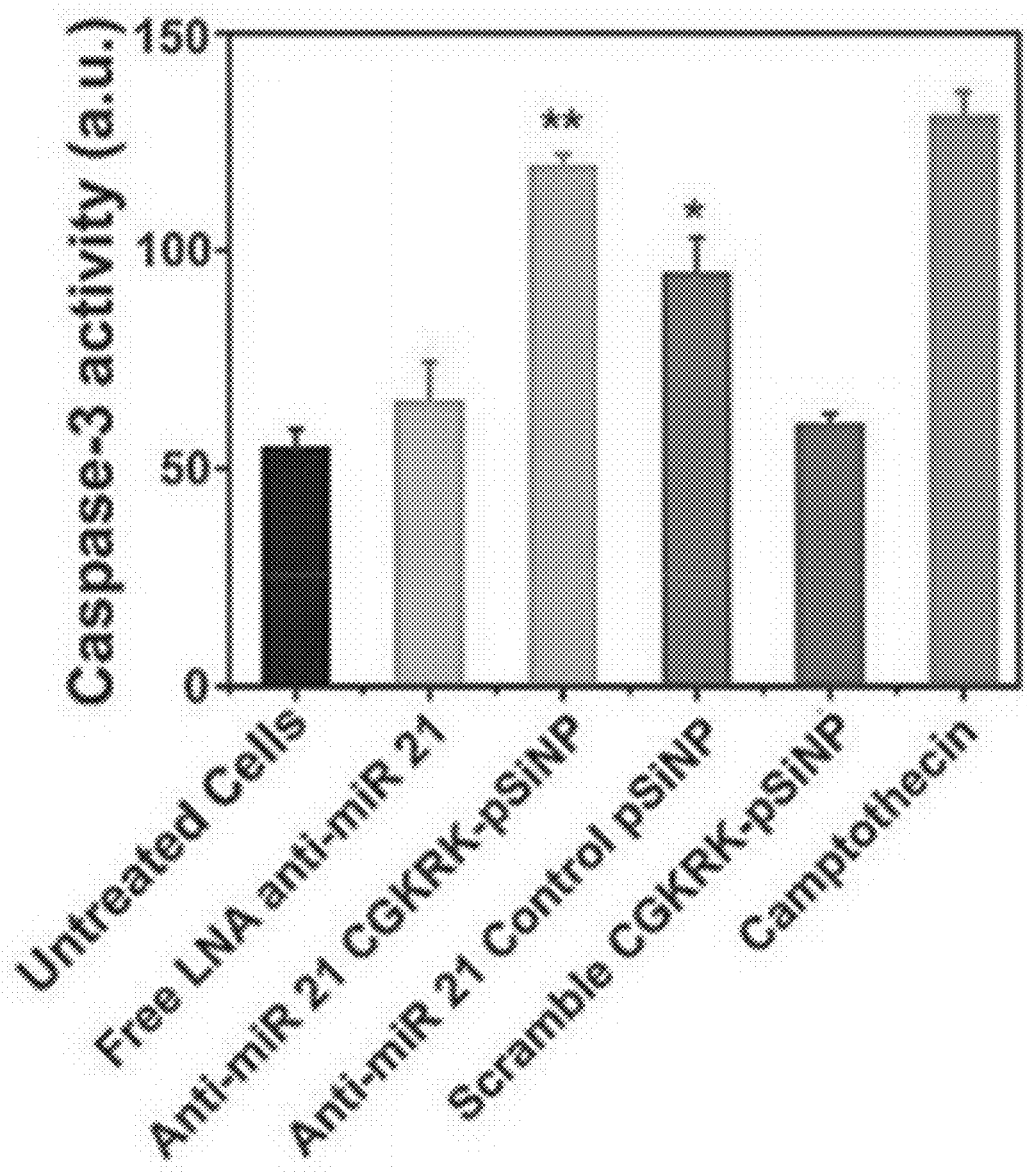
FIG. 2C illustrates the Caspase-3 assay results for confirming an increase in fluorescence intensity from active markers during the induction of apoptosis in OAW42 cells treated with a marked nanoparticle preparation to confirm cytotoxicity in a model OAW42 ovarian cancer cell line (mean±SD, n=6, *p<0.05, ** p<0.01)

In contrast, as illustrated in FIG. 2C, it was confirmed that when cells were treated with free anti-miR-21 LNA loaded with scrambled LNA and CGKRK (SEQ ID NO: 1)-pSiNP loaded with scrambled LNA, Caspase-3 activity was not significantly increased compared to untreated cells.

2-4. Confirmation of Changes in Viability Caused by Silencing of miR-21

An experiment of measuring cell viability was performed by treating OAW42 cells with anti-miR-21 CGKRK (SEQ ID NO: 1)-pSiNP.

Figure 2D:
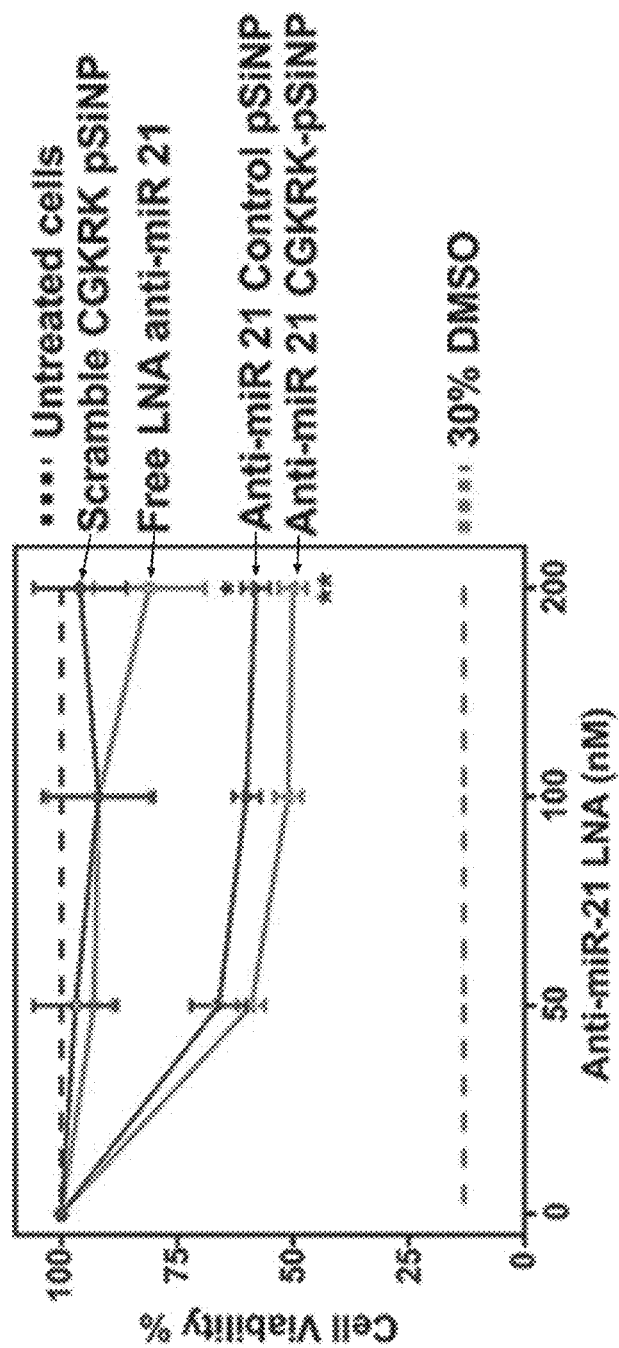
FIG. 2D illustrates the results of confirming the viability (MTT analysis) of OAW42 cells cultured together with a marked nanoparticle preparation in LNA at various concentrations (50 nM, 100 nM, and 200 nM) to confirm cytotoxicity in a model OAW42 ovarian cancer cell line (mean±SD, n=6, *p<0.05, ** p<0.01)

As a result, as illustrated in FIG. 2D, since it was confirmed that treatment of OAW42 cells with anti-miR-21 CGKRK (SEQ ID NO: 1)-pSiNP significantly reduced cell viability (about 50%), a potential therapeutic effect of the anti-miRNA could be predicted.

Furthermore, the dose of anti-miR-21 CGKRK (SEQ ID NO: 1)-pSiNP was set to 0 to 200 nM LNA, and the toxicity of applying the anti-miR-21 CGKRK (SEQ ID NO: 1)-pSiNP preparation was clearly confirmed at a LNA concentration of 50 nM or higher.

Meanwhile, cytotoxicity from free anti-miR-21 LNA (not loaded into porous silicon nanoparticles) was detected only at 200 nM (the highest concentration), and no side effects on viability were observed when the scrambled LNA CGKRK (SEQ ID NO: 1)-pSiNP preparation corresponding to a LNA concentration of 200 nM was used.

Therefore, it was confirmed that the nanoparticle anti-miRNA delivery system itself (without active anti-miRNA payload) does not show cytotoxicity over a LNA concentration range of 0 to 200 nM.

It was confirmed that when a control in which anti-miR-21 LNA was loaded into a pSiNP (LNA concentration of 200 nM) was applied to OAW42 cells, cell viability was reduced by 42%.

When compared with the anti-miR-21 CGKRK (SEQ ID NO: 1)-pSiNP according to the present disclosure, the result of a low decrease in cell viability of the control coincides with the experimental results observed in the RT-qPCR and Caspase activity analysis data.

Example 3. Confirmation of Effects of Anti-miR-21 CGKRK (SEQ ID NO: 1)-pSiNP in Various Ovarian Cancer Cell Lines As describe above, the apoptosis induction effect and cell viability reduction effect of anti-miR-21 CGKRK (SEQ ID NO: 1)-pSiNP were confirmed in an ovarian cancer cell line OAW42, and an attempt was made to evaluate the above effects of anti-miRNA pSiNP in other representative ovarian cancer cell lines.

The goals of the experiment are twofold: 1) confirmation of the most effective cancer cell surface protein-binding peptide, and 2) establishment of a reaction rate for anti-miRNA pSiNP in human ovarian cancer cell panels to select optimal nanoparticle formulations and tumor models for in vivo studies.

In order to achieve the above goals, experiments for evaluating the targeting effect and cell toxicity activity of anti-miR-21 CGKRK (SEQ ID NO: 1)-pSiNP for six ovarian cancer cell lines (CAOV-3, COV-318, OVCAR-8, Kuramochi, KF-28, and IGROV-1) were additionally performed.

3-1. Confirmation of Optimal Cancer Cell Surface Protein-Binding Peptide

To confirm the optimal cancer cell surface protein-binding peptide, each cell line was exposed to the cancer cell surface protein-binding peptide-functionalized pSiNP and the accumulation of nanoparticles in the cells was analyzed by flow cytometry (fluorescence signal from the FAM-labeled peptide).

Figure 4A:
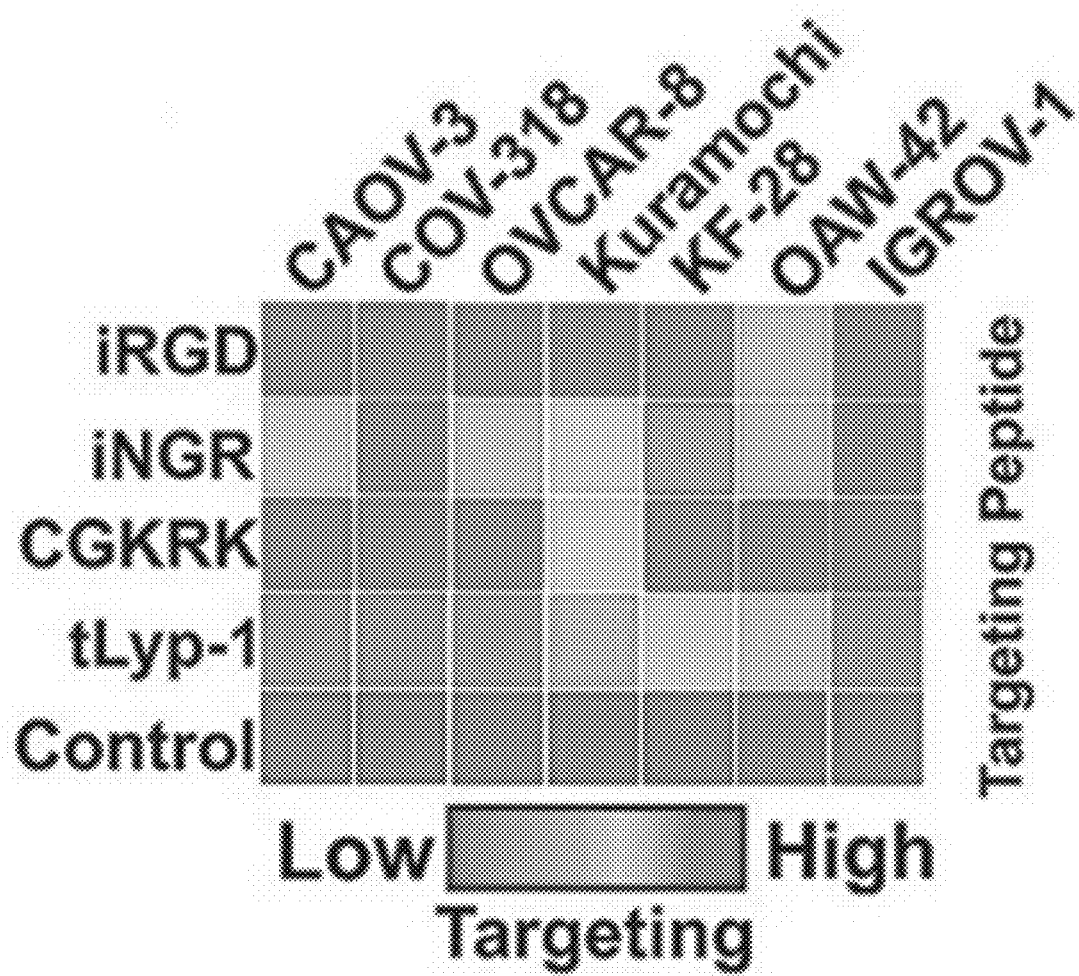
FIG. 4A illustrates the results of culturing an array of ovarian cancer cell lines with pSiNPs functionalized with different FAM-labeled peptides and measuring the fluorescence intensity associated with nanoparticle accumulation by flow cytometry.

As a result, as illustrated in FIG. 4A, it was confirmed that CGKRK (SEQ ID NO: 1)-pSiNP and iRGD-pSiNP generated the strongest fluorescence signal in 5 out of 6 cell lines, meaning that a large amount was accumulated in the cells.

Meanwhile, since CGKRK (SEQ ID NO: 1)-pSiNP was statistically more accumulated in OAW42 cells as described above (see FIG. 2A), based on the miR-21 silencing results obtained from the OAW42 cells, the present inventors selected anti-miR psiNP equipped with a tumor-homing peptide CGKRK (SEQ ID NO: 1) as an anti-miR delivery system for the treatment of ovarian cancer.

3-2. Confirmation of Effects of Anti-miR-21 CGKRK (SEQ ID NO: 1)-pSiNP on Viability of Ovarian Cancer Cell Line Effects of anti-miR-21CGKRK (SEQ ID NO: 1)-pSiNP on the survival of other ovarian cancer cell lines were investigated.

Figure 4B:
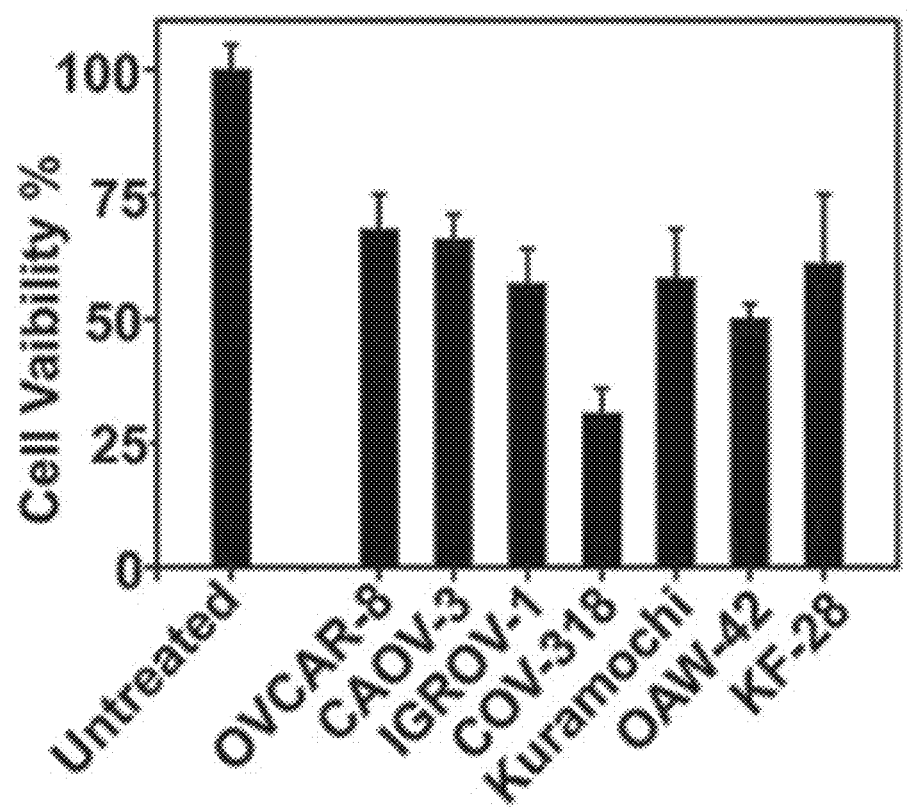
FIG. 4B illustrates the results of analyzing the viability (MTT assay) of different cell lines cultured together with anti-miR-21 CGKRK (SEQ ID NO: 1)-pSiNP.

As a result, as illustrated in FIG. 4B, it was confirmed that most cell lines treated with the anti-miR-21CGKRK (SEQ ID NO: 1)-pSiNP (LNA concentration was 200 nM) showed a decrease in viability in a range of 30 to 50%.

In addition, among the cell lines tested above, since the survival rate of COV-318 cells was reduced by 65% or more, it was confirmed that the COV-318 cells were the most vulnerable to the application of anti-miR-21CGKRK (SEQ ID NO: 1)-pSiNP.

Meanwhile, to confirm the correlation between the decrease in cell viability and the decrease in miR-21 expression, RT-qPCR was performed on cells treated with anti-miR-21CGKRK (SEQ ID NO: 1)-pSiNP.

Figure 4C:
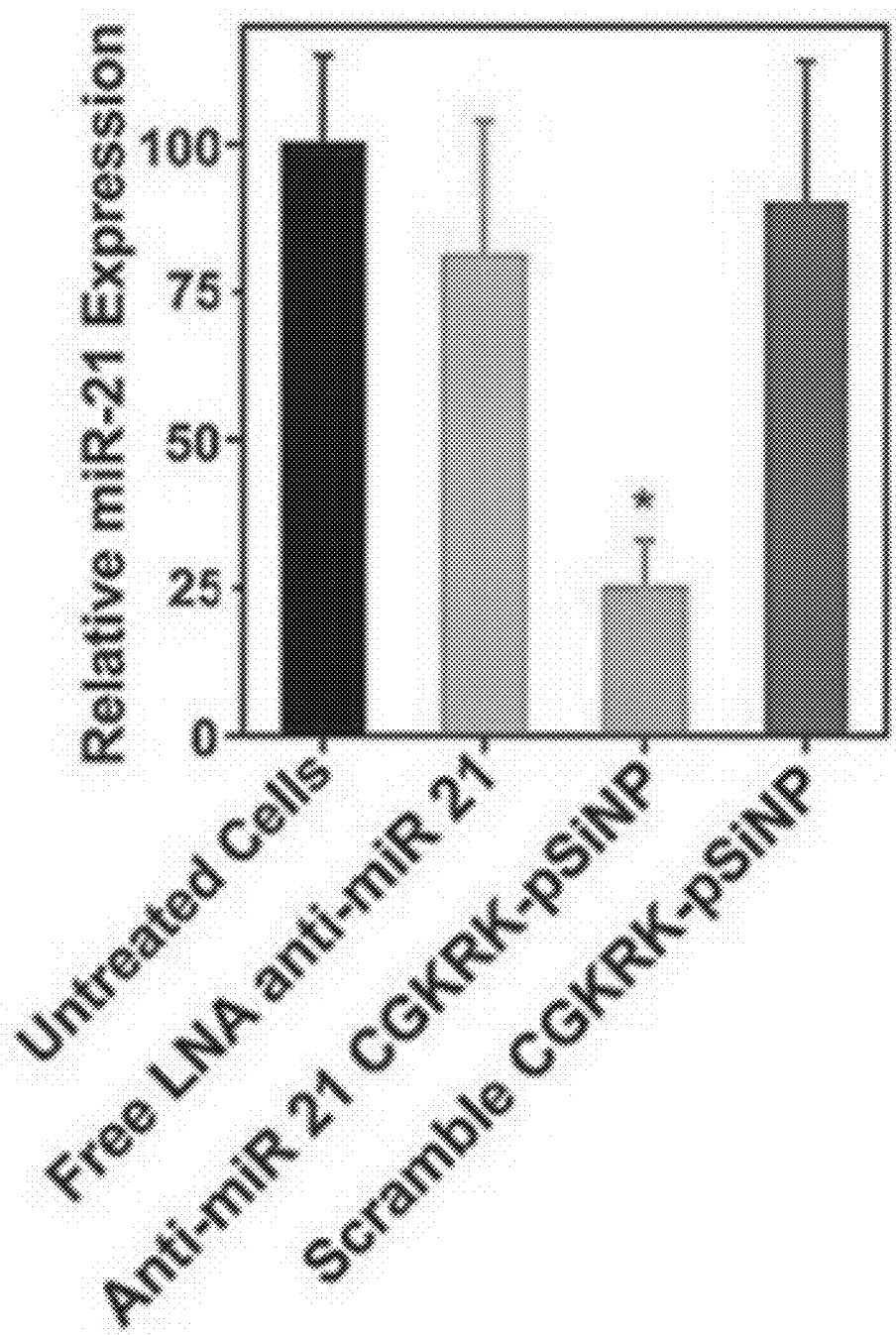
FIG. 4C illustrates the RT-qPCR results of miR-21 in COV-318 cells treated with a marked nanoparticle preparation (mean±SD, n=6, *p<0.05)

As a result, as illustrated in FIG. 4C, it was confirmed that the anti-miR-21 CGKRK (SEQ ID NO: 1)-pSiNP treatment reduced the relative expression of miR-21 by about 75%. The results confirm that pSiNP promotes silencing of a target miRNA and correlates with the decrease in cell viability.

Furthermore, it was confirmed that the treatment with free anti-miR-21 LNA did not induce statistically significant silencing of miR-21, and as illustrated in FIG. 4C, it was confirmed that, when cells treated with CGKRK (SEQ ID NO: 1)-pSiNP loaded with scrambled LNA were compared with untreated cells as a control, no difference was observed in the non-specific miR-21 knockdown.

Further, the specificity of tumor cell targeting for healthy cells was evaluated by comparing the uptake of FAM-labeled CGKRK (SEQ ID NO: 1)-pSiNP into COV-318 cancer cells with the uptake in normal human peritoneal mesothelial LP-9 cells.

Figure 4D:
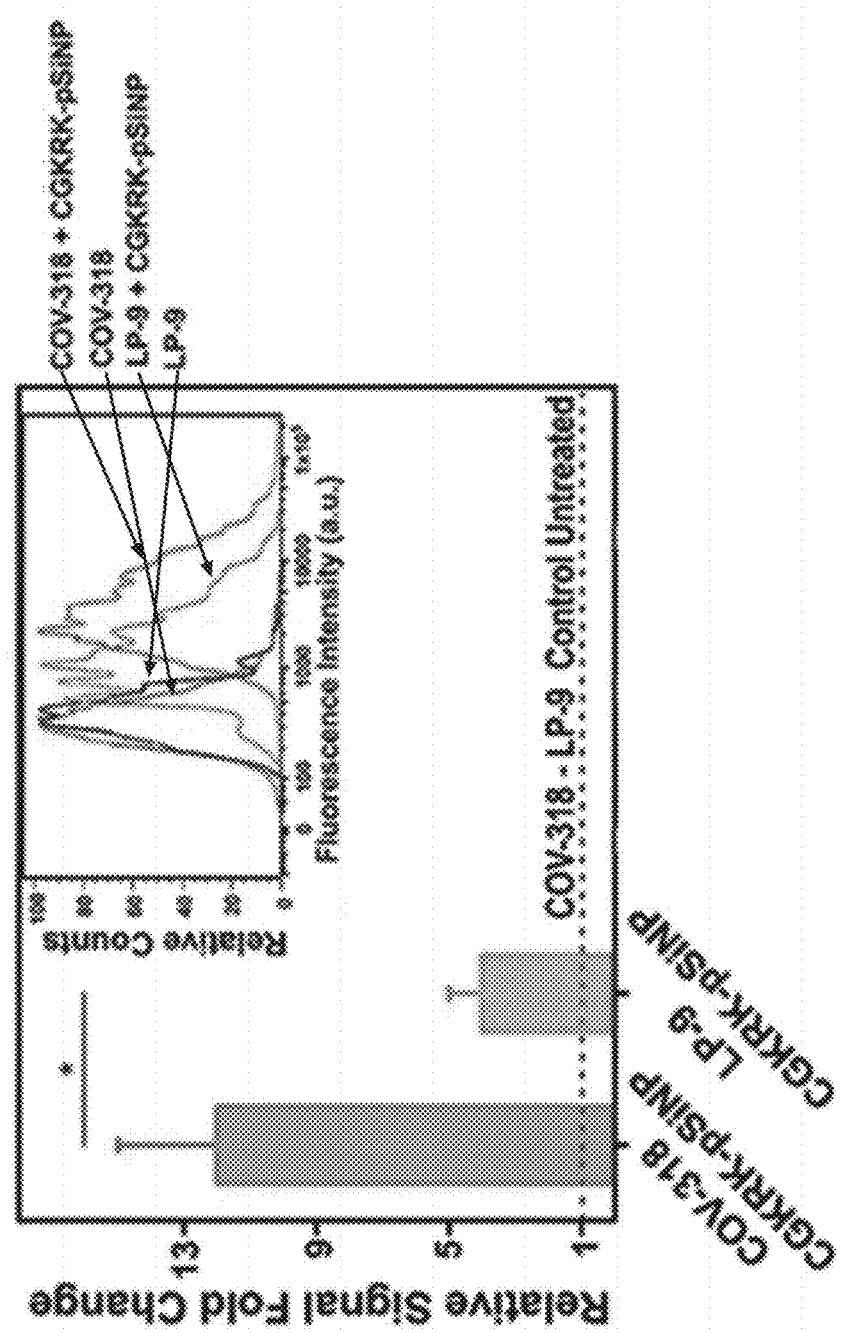
FIG. 4D illustrates the results of relative signal fold changes in fluorescence signals measured by flow cytometry in COV-318 and LP-9 cells cultured together with FAM-labeled CGKRK (SEQ ID NO: 1)-pSiNP, and the inset shows the results of confirming a representative cell analysis profile for the marked preparation (mean±SD, n=3, * p<0.05)

As a result, as illustrated in FIG. 4D, it was confirmed that, when quantified by the intensity of the FAM signal, CGKRK (SEQ ID NO: 1)-pSiNP was uptaken 4-fold more efficiently by COV-318 cells compared to LP-9 cells.

Example 4. Confirmation of Effects of Anti-miR21 CGKRK (SEQ ID NO: 1)-pSiNP in Tumor-Xenografted Mice Using the confirmed optimal cells and cancer cell surface protein-binding peptides, the in vivo efficacy of anti-miRNA pSiNP was confirmed using COV-318 xenograft tumors subcutaneously transplanted into nude mice.

4-1. Evaluation of Biodistribution of Nanoparticles in Tumor-Xenografted Mice

First, the biodistribution of nanoparticles was evaluated in tumor-bearing mice.

More specifically, an experiment was performed by intravenously injecting of any one selected from the group of the following into the tumor-bearing mice.

(i) saline as a negative control;
(ii) pSiNP SiNP functionalized with a control CRA (Cys-Arg-Ala) peptide; and
(iii) Targeting CGKRK (SEQ ID NO: 1)-pSiNP.

The cationic CRA peptide was chosen as a control peptide for in vivo studies and its short sequence was chosen because it is unlikely to contain any potential targeting motifs for the in vivo environment.

As a result, it was confirmed that, when both a non-functionalized pSiNP having no conjugated peptide and a PEGylated pSiNP having no conjugated peptide were compared with the cancer cell surface protein-binding peptide-pSiNP, there was no organ-specific accumulation in mice.

In addition, in the present disclosure, the present inventors conducted experiments using more stringent control nanoparticles by introducing a non-cancer cell surface protein-binding peptide exhibiting a net positive charge similar to the cancer cell surface protein-binding peptide CGKRK (SEQ ID NO: 1). This allows the control nanoparticle structure to have physicochemical characteristics which are more similar to those of the nanoparticle structure of the selected targeting pSiNP, thereby clearly confirming that the observed difference in vivo (that is, organ-specific accumulation) results from the sequence-specific targeting efficacy of the CGKRK (SEQ ID NO: 1) peptide.

To simultaneously evaluate the stability of the nanoparticle system and track individual components in vivo, biodistribution studies using a dual-labeled nanoparticle structure were conducted, where (1) the payload was a Quasar 670-labeled anti-miR-21 oligonucleotide and (2) the peptide attached to the outer surface of the particles was labeled with FAM. Next, the integrity of the in vivo nanosystem could be evaluated by recording the fluorescence intensities of both the payload and the pSiNP-attached peptide in each excised organ.

As a result, as illustrated in FIG. 4A, through an analysis of red Quasar 670 fluorescence emission from excised organs, it was confirmed that a significant amount of the oligonucleotide payload was accumulated in mice administered CGKRK (SEQ ID NO: 1)-pSiNP.

Furthermore, it was confirmed that the fluorescence emission (n=6) from the tumors excised from the mice was 3-fold stronger than that in the saline injection control mouse.

Figure 5A:
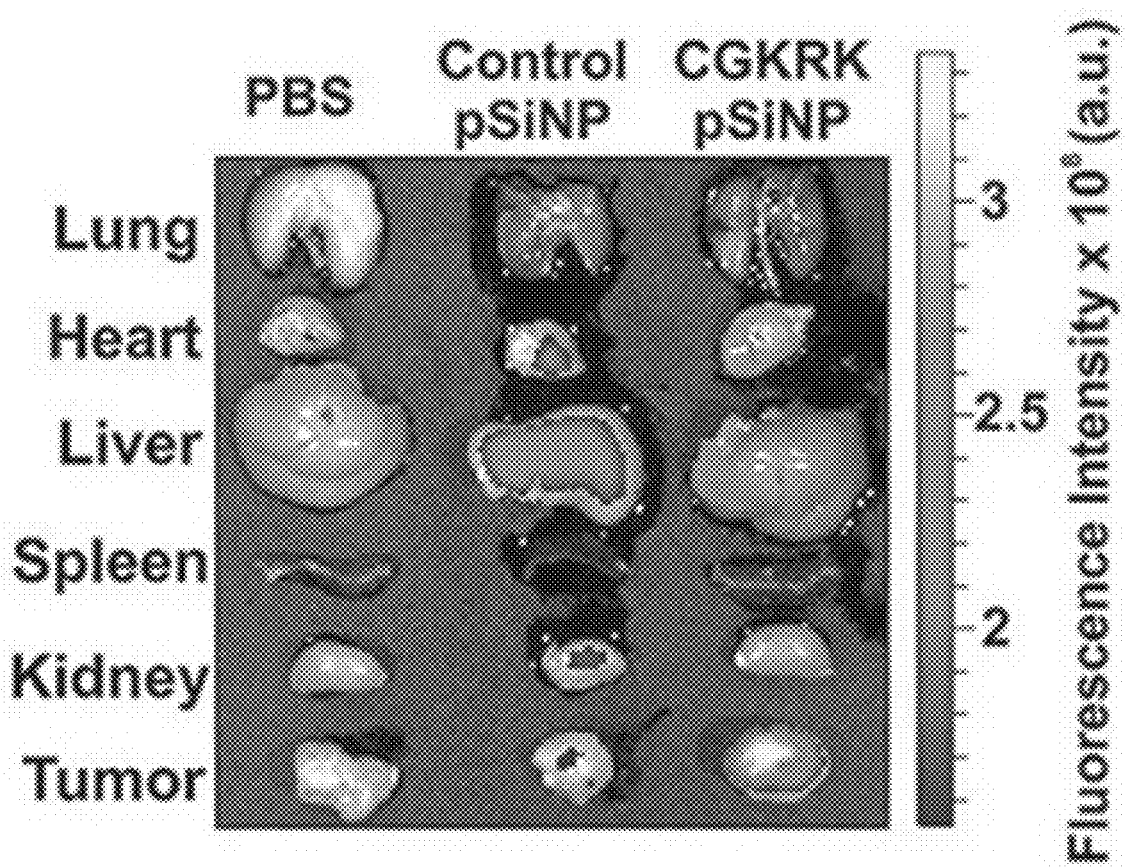
FIG. 5A illustrates the results of confirming the biodistribution of targeted and non-targeted nanoparticles in nude mice bearing subcutaneous COV-318 xenograft tumors to track a Quasar 670-labeled anti-miR-21 oligonucleotide payload, and illustrates an ex vivo fluorescence image of organs excised after saline intravenous injection of tumor-targeting CGKRK (SEQ ID NO: 1)-pSiNP into which a negative control group (PBS column), non-cancer cell surface protein-binding peptide CRA-containing Quasar 670-labeled anti-miR-21 oligonucleotides (Control pSiNP column) and Quasar 670-labeled anti-miR-21 oligonucleotides (CGKRK (SEQ ID NO: 1)PSiNP column-) are loaded.
Figure 5B:
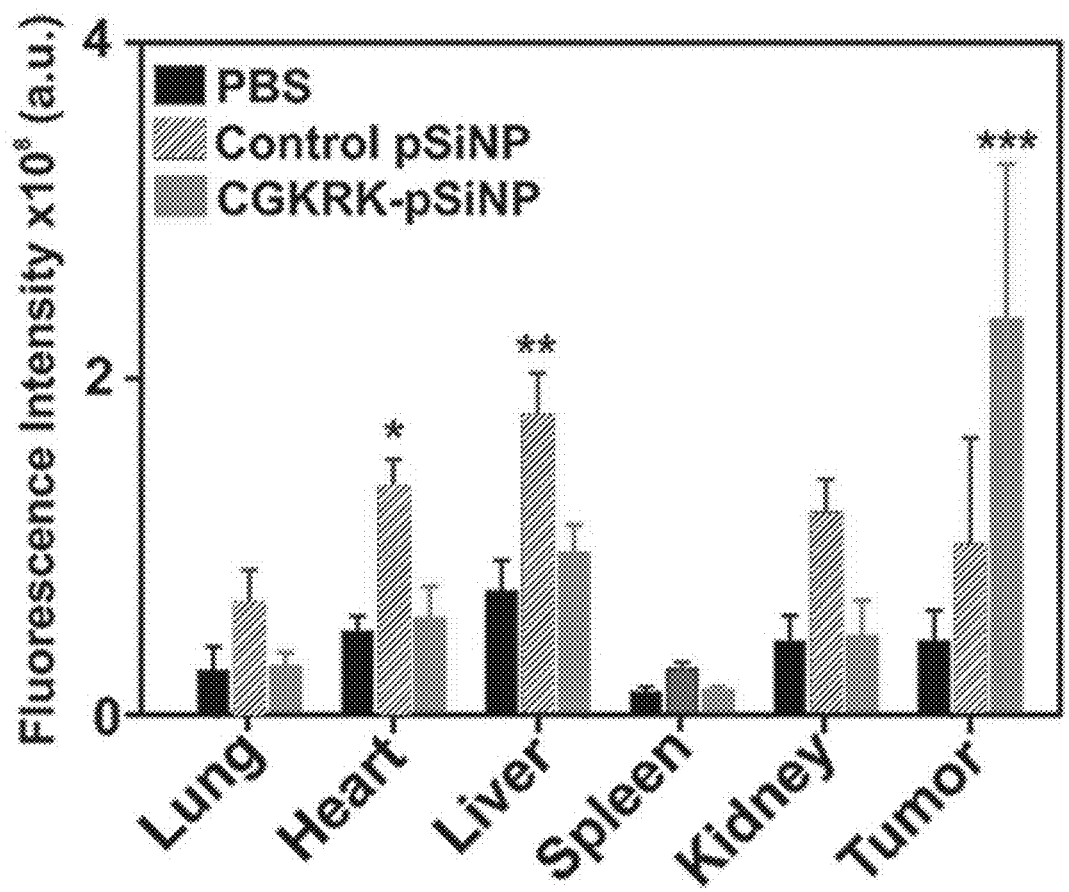
FIG. 5B illustrates the results of confirming the biodistribution of targeted and non-targeted nanoparticles in excised organs of nude mice bearing subcutaneous COV-318 xenograft tumors to track a Quasar 670-labeled anti-miR-21 oligonucleotide payload, and illustrates the results of quantifying the fluorescence signal of the Quasar 670-labeled oligonucleotide payload.

Further, as illustrated in FIGS. 5A and 5B, it was confirmed that CGKRK (SEQ ID NO: 1)-pSiNP was significantly more accumulated in tumors than in other organs when compared with the control CRA-pSiNP.

The experimental results coincided with the ability of the target peptide CGKRK (SEQ ID NO: 1) to improve the accumulation of nanoparticles in tumors.

4-2. Confirmation of Effects of Anti-miR21 CGKRK (SEQ ID NO: 1)-pSiNP in Tumor-Xenografted Mice The in vivo therapeutic efficacy of the anti-miRNA pSiNP preparation for the COV-318 xenograft tumor model was evaluated.

All used nanoparticle preparations were stored in pure ethanol at 4° C. for at least 7 days before administration to mice, and the particles were separated from an ethanol solvent by centrifugation, resuspended in PBS, and immediately used. A therapy consisting of a total of 5 doses given on days 0, 1, 3, 5 and 7 was injected into mice through the tail vein, which followed an administration protocol used for another anti-m iRNA.

Figure 6A:
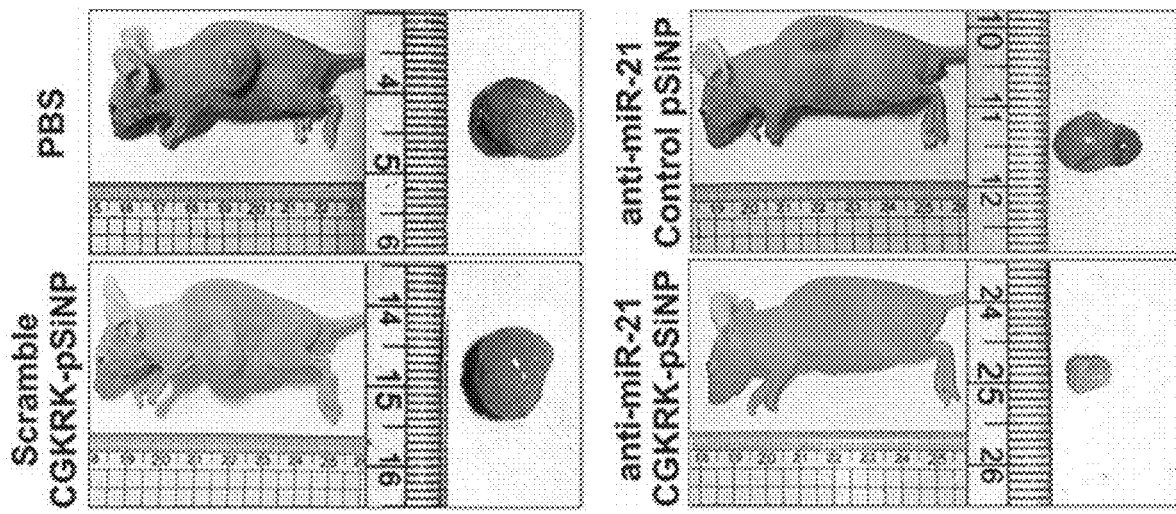
FIG. 6A illustrates a set of images of tumors excised 10 days after a first injection after administrating a marked preparation to nude mice bearing subcutaneous COV-318 xenograft tumors.

As a result, as illustrated in FIG. 6A, it was confirmed that the tumors excised from the mice treated with anti-miR-21CGKRK (SEQ ID NO: 1)-pSiNP were completely suppressed in growth, and the total volume of the tumors was not increased during the 10-day evaluation.

Figure 6B:
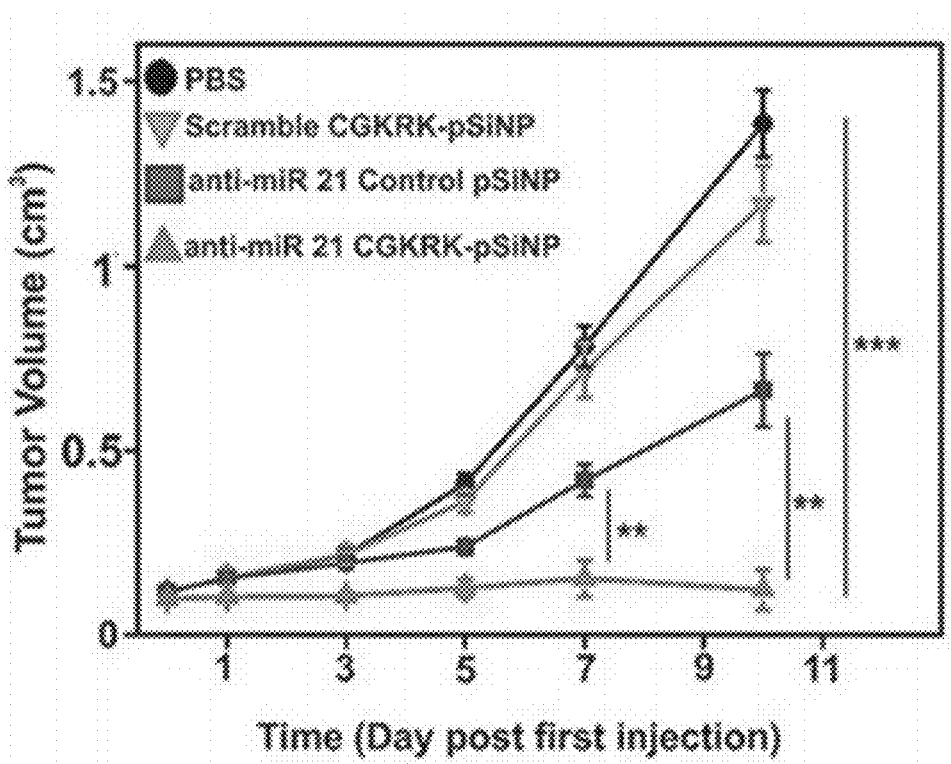
FIG. 6B illustrates a tumor volume growth curve after intravenous injection of different nanoparticle preparations into nude mice bearing subcutaneous COV-318 xenograft tumors (mean±SEM, n=6-7 per group,  p<0.01, * p<0.001)

In contrast, as illustrated in FIG. 6B, it was confirmed that for the control tumor-bearing mice administered PBS loaded with a scrambled LNA sequence or CGKRK (SEQ ID NO: 1)-pSiNP loaded with a scrambled LNA sequence, the tumor volume was increased 10-fold over the same time period.

Although it was confirmed that the administration of a control preparation of CRA-pSiNP which contained anti-miR-21 LNA, but was non-targeted, induced a slight reduction in tumor growth, it exhibited a significantly lower treatment effect (tumor growth inhibition) than that of the anti-miR-21 CGKRK (SEQ ID NO: 1)-pSiNP (p<0.01).

Meanwhile, to confirm that tumor growth inhibition is associated with miR-21 silencing, the knockdown of the target miR-21 was quantified using a tumor tissue excised from mice treated with anti-miR-21 CGKRK (SEQ ID NO: 1)-pSiNP to perform RT-qPCR.

Figure 6C:
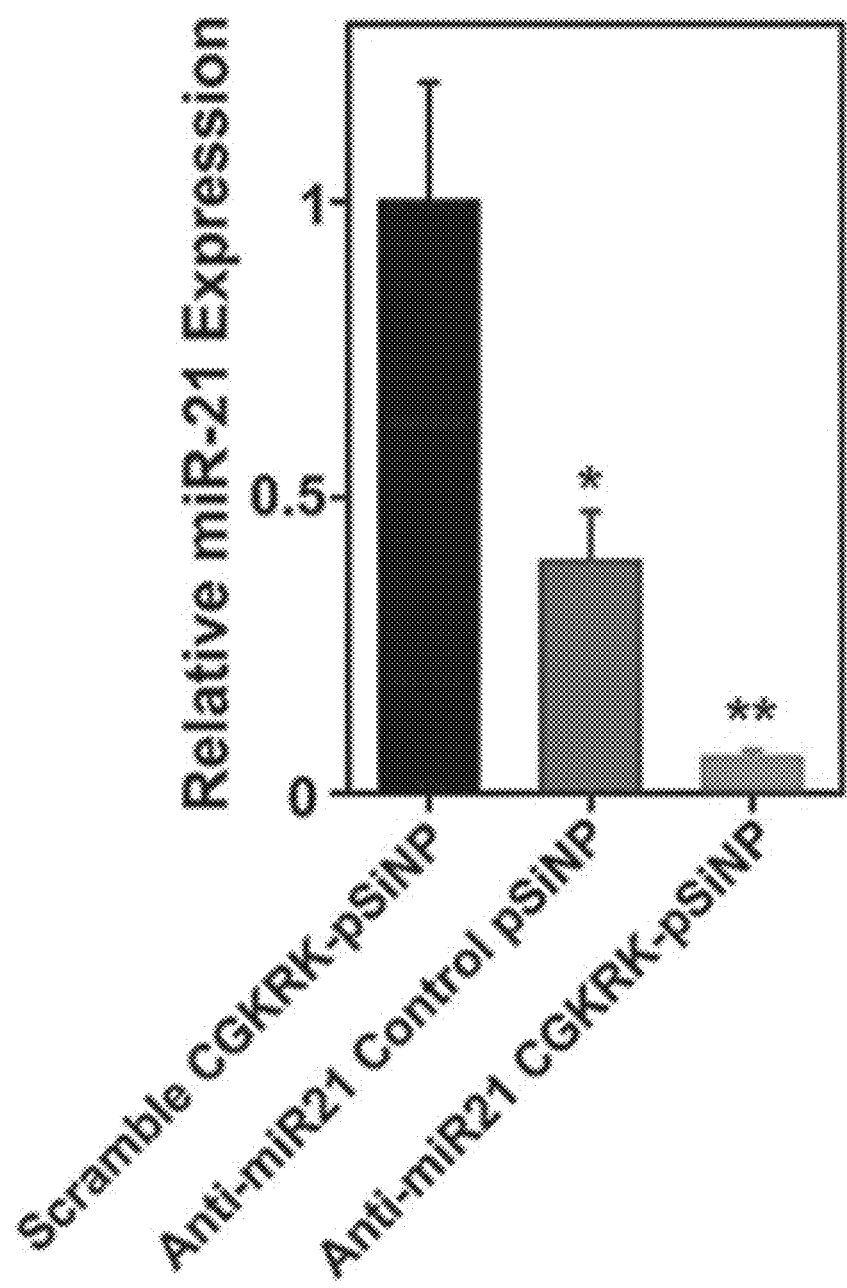
FIG. 6C illustrates the RT-qPCR results of miR-21 extracted from mouse tumors 10 days after treatment by administration of the marked nanoparticle preparation (mean±SEM, n=6-7 per group, mean for 3 technical replicates, * p<0.05, ** p<0.01)

As a result, as illustrated in FIG. 6C, it was confirmed that tumors excised from mice administered anti-miR-21 CGKRK (SEQ ID NO: 1)-pSiNP had reduced miR-21 expression compared to tumors excised from mice administered scrambled LNACGKRK (SEQ ID NO: 1)-pSiNP, and the observed effects were similar to those obtained from cell culture experiments (in vitro). The experimental results confirm an effective miR-21 silencing effect of anti-miR-21 CGKRK (SEQ ID NO: 1)-pSiNP in tumors.

Figure 6D:
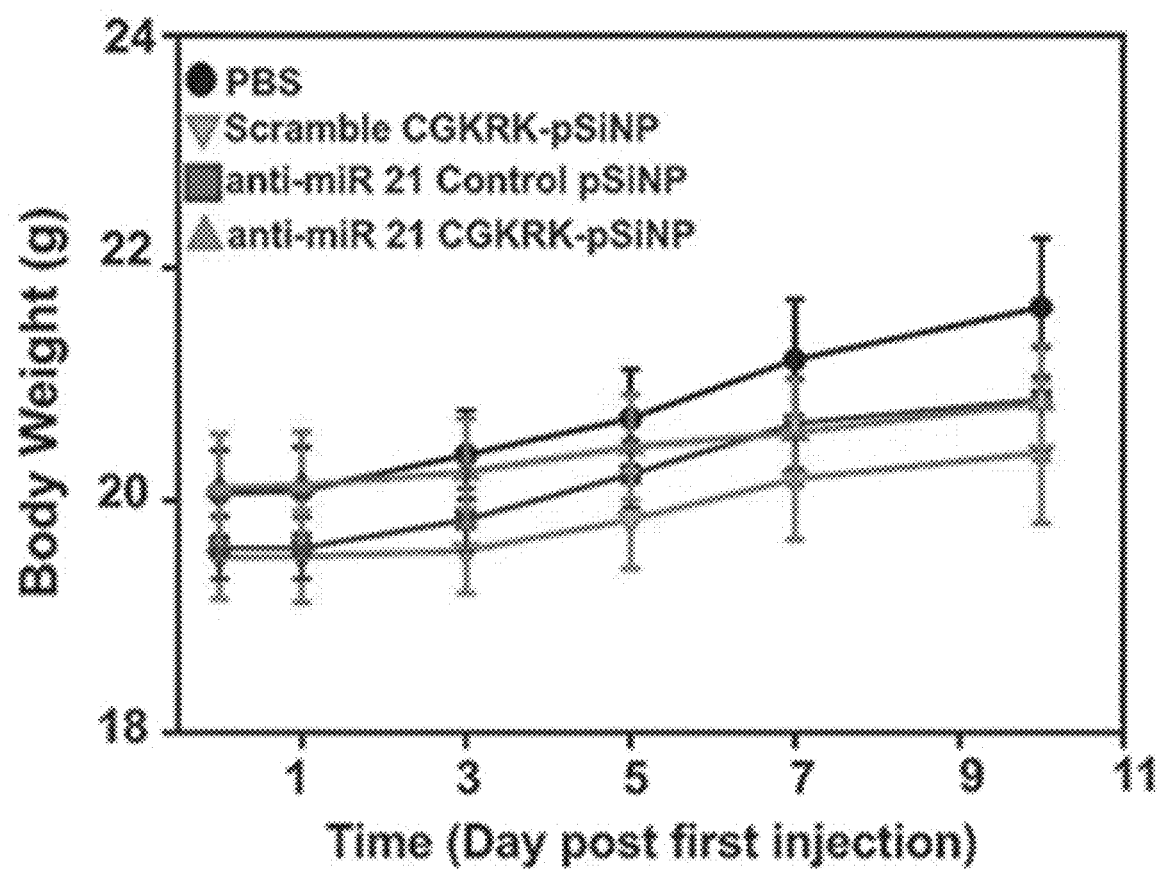
FIG. 6D illustrates the change in body weight of tumor-bearing mice during treatment with the marked nanoparticle preparation (mean±SEM, n=6-7 per group).

In addition, as illustrated in FIG. 6D, the average body weight of mice gradually increased during all treatment processes, there was no substantial difference between any cohorts, and there was no drastic reduction in weight, which could indicate acute toxicity of the anti-miRNA preparation.

As a result of intensive studies in order to use and apply anti-miR-21 oligonucleotides to the treatment of cancer, the present inventors confirmed that when porous silicon nanoparticles containing an anti-miRNA-21 oligonucleotide to which a specific cancer cell surface protein-binding peptide is conjugated are applied, apoptosis is induced in an ovarian cancer cell line and cell viability is reduced, thus, an anti-miRNA delivery system, which is the aforementioned conjugate, is expected to be usefully used for as a platform for treating various cancers, especially for treating ovarian cancer.

The above-described description of the present disclosure is provided for illustrative purposes, and those skilled in the art to which the present disclosure pertains will understand that the present disclosure can be easily modified into other specific forms without changing the technical spirit or essential features of the present disclosure. Therefore, it should be understood that the above-described embodiments are illustrative in all aspects and are not restrictive.

INDUSTRIAL APPLICABILITY

Since it was confirmed that when porous silicon nanoparticles containing an anti-miRNA-21 oligonucleotide to which the specific cancer cell surface protein-binding peptide of the present disclosure is conjugated are applied, apoptosis is induced in an ovarian cancer cell line and cell viability is reduced, an anti-miRNA delivery system, which is the aforementioned conjugate, is expected to be usefully used as a platform for treating various cancers, especially for treating ovarian cancer.

This application contains references to amino acid sequences and/or nucleic acid sequences which have been submitted concurrently herewith as the sequence listing text file entitled "000044_SequenceListing.TXT", file size 1.36 KiloBytes (KB), created on 25 Oct. 2022. The aforementioned sequence listing is hereby incorporated by reference in its entirety pursuant to 37 C.F.R. § 1.52(e)(5).

What is claimed is:

1. A cancer-targeting anti-miRNA delivery system comprising:
   a cancer cell surface protein-binding peptide comprising an amino acid sequence represented by SEQ ID NO: 1; and
   porous silicon nanoparticles (pSiNP) containing anti-miR-21 comprising a nucleotide sequence represented by SEQ ID NO: 2.

2. The cancer-targeting anti-miRNA delivery system of claim 1, wherein the cancer cell surface protein-binding peptide binds to a cell surface protein p32.

3. A method for treating cancer, the method comprising administering, to an individual, a pharmaceutical composition comprising: a cancer cell surface protein-binding peptide comprising an amino acid sequence represented by SEQ ID NO: 1; and porous silicon nanoparticles (pSiNP) containing anti-miR-21 comprising a nucleotide sequence represented by SEQ ID NO: 2, as active ingredients.

4. A method for preparing a cancer-targeting anti-miRNA delivery system, the method comprising:
   1) loading anti-miRNA into porous silicon nanoparticles by mixing the anti-miRNA, a CaCl$_2$) solution, and porous silicon nanoparticles; and 2) modifying the surface of the porous silicon particles of the product in 1) with a cancer cell protein-binding peptide.

* * * * *